(12) United States Patent
Van Bladel et al.

(10) Patent No.: US 10,314,498 B2
(45) Date of Patent: Jun. 11, 2019

(54) CARDIAC TISSUE PENETRATING DEVICES, METHODS, AND SYSTEMS FOR TREATMENT OF CONGESTIVE HEART FAILURE AND OTHER CONDITIONS

(71) Applicant: BioVentrix, Inc., San Ramon, CA (US)

(72) Inventors: Kevin Van Bladel, San Ramon, CA (US); Meir Moshe, El Sobrante, CA (US); Lon Annest, New York, NY (US)

(73) Assignee: BioVentrix, Inc., San Ramon, CA (US)

( * ) Notice: Subject to any disclaimer, the term of this patent is extended or adjusted under 35 U.S.C. 154(b) by 1082 days.

(21) Appl. No.: 14/282,849

(22) Filed: May 20, 2014

(65) Prior Publication Data

US 2014/0350417 A1 Nov. 27, 2014

Related U.S. Application Data

(60) Provisional application No. 61/827,114, filed on May 24, 2013.

(51) Int. Cl.
*A61F 2/24* (2006.01)
*A61B 5/0215* (2006.01)
(Continued)

(52) U.S. Cl.
CPC .......... *A61B 5/0215* (2013.01); *A61B 1/0058* (2013.01); *A61B 5/065* (2013.01);
(Continued)

(58) Field of Classification Search
CPC .................. A61F 2/2478; A61F 2/2487; A61F 2002/249; A61B 17/0487;
(Continued)

(56) References Cited

U.S. PATENT DOCUMENTS 3,737,579 A 6/1973 Bolduc
4,010,758 A 3/1977 Rockland et al.
(Continued)

FOREIGN PATENT DOCUMENTS

EP 1078644 A1 2/2001
WO 00/06028 A1 2/2000
(Continued)

OTHER PUBLICATIONS

European Examination Report of EP Patent Application 05810316.9 dated Mar. 10, 2009, 6 pages.
(Continued)

*Primary Examiner* — Carrie R Dorna
(74) *Attorney, Agent, or Firm* — Kilpatrick Townsend & Stockton LLP

(57) ABSTRACT

According to one embodiment, a tissue penetrating device includes an elongate shaft having a proximal end, a distal end, and a lumen extending there between. A first needle is disposed within the lumen of the elongate shaft and is extendable therefrom between a first configuration and a second configuration. In the first configuration, the first needle is disposed within the elongate shaft's lumen and is substantially aligned with an axis of the lumen. In the second configuration, the first needle extends distally of the elongate shaft's distal end and bends away from the lumen's axis. A second needle is disposed within a lumen of the first needle and is extendable therefrom when the first needle is positioned in the first configuration and when the first needle is positioned in the second configuration. The second needle may be extended from the first needle to penetrate tissue of a patient.

24 Claims, 18 Drawing Sheets

(51) Int. Cl.
  *A61B 1/005* (2006.01)
  *A61B 5/06* (2006.01)
  *A61B 17/04* (2006.01)
  *A61B 17/00* (2006.01)
  *A61B 17/06* (2006.01)

(52) U.S. Cl.
  CPC ........ *A61F 2/2487* (2013.01); *A61B 17/0487* (2013.01); *A61B 2017/00243* (2013.01); *A61B 2017/00247* (2013.01); *A61B 2017/0409* (2013.01); *A61B 2017/0417* (2013.01); *A61B 2017/06052* (2013.01); *A61F 2002/249* (2013.01)

(58) Field of Classification Search
  CPC .. A61B 2017/00243; A61B 2017/0409; A61B 17/3478
  See application file for complete search history.

(56) References Cited

U.S. PATENT DOCUMENTS

| | | |
|---|---|---|
| 4,007,743 A | 12/1977 | Blake |
| 4,313,448 A | 2/1982 | Stokes |
| 4,357,946 A | 11/1982 | Dutcher et al. |
| 4,991,578 A | 2/1991 | Cohen |
| 5,139,033 A | 8/1992 | Everett |
| 5,246,014 A | 9/1993 | Williams et al. |
| 5,295,958 A | 3/1994 | Shturman |
| 5,336,252 A | 8/1994 | Cohen |
| 5,464,447 A | 11/1995 | Fogarty et al. |
| 5,482,037 A | 1/1996 | Borghi |
| 5,484,445 A | 1/1996 | Knuth |
| 5,522,875 A | 6/1996 | Gates et al. |
| 5,553,612 A | 9/1996 | Lundback |
| 5,575,814 A | 11/1996 | Giele et al. |
| 5,716,391 A | 2/1998 | Grandjean |
| 5,716,392 A | 2/1998 | Bourgeois et al. |
| 5,755,697 A | 5/1998 | Jones et al. |
| 5,792,217 A | 8/1998 | Camps et al. |
| 5,810,884 A | 9/1998 | Kim |
| 5,827,216 A | 10/1998 | Igo et al. |
| 5,830,224 A | 11/1998 | Cohn et al. |
| 5,865,730 A | 2/1999 | Fox et al. |
| 5,868,770 A | 2/1999 | Rygaard |
| 5,871,352 A | 2/1999 | Schroeppel |
| 5,871,528 A | 2/1999 | Camps et al. |
| 5,897,584 A | 4/1999 | Herman |
| 5,902,331 A | 4/1999 | Bonner et al. |
| 5,902,234 A | 5/1999 | Thompson et al. |
| 5,961,440 A | 10/1999 | Schweich, Jr. et al. |
| 5,972,013 A | 10/1999 | Schmidt |
| 6,010,476 A | 1/2000 | Saadat |
| 6,010,526 A | 1/2000 | Sandstrom et al. |
| 6,045,497 A | 4/2000 | Schweich et al. |
| 6,050,936 A | 4/2000 | Schweich, Jr. et al. |
| 6,059,715 A | 5/2000 | Schweich, Jr. et al. |
| 6,080,175 A | 6/2000 | Hogendijk |
| 6,080,182 A | 6/2000 | Shaw et al. |
| 6,125,852 A | 10/2000 | Stevens et al. |
| 6,132,456 A | 10/2000 | Sommer et al. |
| 6,155,968 A | 12/2000 | Wilk |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,166,684 A | 12/2000 | Yoshikawa et al. |
| 6,185,464 B1 | 2/2001 | Bonner et al. |
| 6,193,652 B1 | 2/2001 | Berky et al. |
| 6,219,579 B1 | 4/2001 | Bakels et al. |
| 6,231,518 B1 | 5/2001 | Grabek et al. |
| 6,258,021 B1 | 7/2001 | Wilk |
| 6,260,552 B1 | 7/2001 | Mortier et al. |
| 6,406,420 B1 | 6/2002 | McCarthy et al. |
| 6,494,825 B1 | 12/2002 | Talpade |
| 6,511,416 B1 | 1/2003 | Green et al. |
| 6,572,529 B2 | 6/2003 | Wilk |
| 6,616,684 B1 | 9/2003 | Vidlund et al. |
| 6,623,508 B2 | 9/2003 | Shaw et al. |
| 6,705,988 B2 | 3/2004 | Spence et al. |
| 6,709,382 B1 | 3/2004 | Horner |
| 6,723,038 B1 | 4/2004 | Schroeder et al. |
| 6,746,471 B2 | 6/2004 | Mortier et al. |
| 6,776,754 B1 | 8/2004 | Wilk |
| 6,808,488 B2 | 10/2004 | Mortier |
| 6,859,662 B2 | 2/2005 | Bombardini |
| 6,890,295 B2 | 5/2005 | Michels et al. |
| 7,146,225 B2 | 12/2006 | Guenst et al. |
| 7,326,177 B2 | 2/2008 | Williamson |
| 7,390,329 B2 | 6/2008 | Westra et al. |
| 7,431,691 B1 | 10/2008 | Wilk |
| 7,637,924 B2 | 12/2009 | Gifford et al. |
| 7,722,523 B2 | 5/2010 | Mortier et al. |
| 7,753,923 B2 | 7/2010 | St. Goar et al. |
| 7,766,816 B2 | 8/2010 | Chin et al. |
| 7,785,248 B2 | 8/2010 | Annest et al. |
| 7,942,854 B1 | 5/2011 | Von Oepen et al. |
| 8,066,766 B2 | 11/2011 | To et al. |
| 8,123,668 B2 | 2/2012 | Annest et al. |
| 8,268,009 B2 | 9/2012 | Teitelbaum et al. |
| 8,394,008 B2 | 3/2013 | Annest et al. |
| 8,425,402 B2 | 4/2013 | Annest et al. |
| 8,449,442 B2 | 5/2013 | Annest et al. |
| 8,491,455 B2 | 7/2013 | Annest et al. |
| 8,506,474 B2 | 8/2013 | Chin et al. |
| 8,636,639 B2 | 1/2014 | Annest et al. |
| 8,968,175 B2 | 3/2015 | Annest et al. |
| 8,979,750 B2 | 3/2015 | Bladel et al. |
| 8,986,189 B2 | 3/2015 | Chin et al. |
| 9,039,594 B2 | 5/2015 | Annest et al. |
| 9,044,231 B2 | 6/2015 | Annest et al. |
| 9,095,363 B2 | 8/2015 | Bladel et al. |
| 9,119,720 B2 | 9/2015 | Chin et al. |
| 9,173,711 B2 | 11/2015 | Butler et al. |
| 9,173,712 B2 | 11/2015 | Annest et al. |
| 9,211,115 B2 | 12/2015 | Annest et al. |
| 9,259,319 B2 | 2/2016 | Chin et al. |
| 9,402,722 B2 | 8/2016 | Annest et al. |
| 2001/0025171 A1 | 9/2001 | Mortier et al. |
| 2001/0041821 A1 | 11/2001 | Wilk |
| 2002/0058855 A1 | 5/2002 | Schweich, Jr. et al. |
| 2002/0077524 A1 | 6/2002 | Schweich, Jr. et al. |
| 2002/0077655 A1 | 6/2002 | Frova |
| 2002/0120298 A1 | 8/2002 | Kramer et al. |
| 2002/0123768 A1 | 9/2002 | Gilkerson et al. |
| 2002/0169359 A1 | 11/2002 | McCarthy et al. |
| 2002/0169360 A1 | 11/2002 | Taylor et al. |
| 2002/0169377 A1* | 11/2002 | Khairkhahan ... A61B 17/32037 600/433 |
| 2002/0188170 A1 | 12/2002 | Santamore et al. |
| 2002/0198563 A1 | 12/2002 | Gainor et al. |
| 2003/0032979 A1 | 2/2003 | Mortier et al. |
| 2003/0163165 A1 | 8/2003 | Bornzin et al. |
| 2003/0166992 A1 | 9/2003 | Schweich, Jr. et al. |
| 2003/0181928 A1 | 9/2003 | Vidlund et al. |
| 2003/0181951 A1 | 9/2003 | Cates |
| 2003/0212446 A1 | 11/2003 | Kaplan et al. |
| 2003/0220587 A1 | 11/2003 | Swenson |
| 2003/0233022 A1 | 12/2003 | Vidlund et al. |
| 2004/0064143 A1 | 4/2004 | Hicken et al. |
| 2004/0082837 A1 | 4/2004 | Willis |
| 2004/0088035 A1 | 5/2004 | Guenst et al. |
| 2004/0138526 A1 | 7/2004 | Guenst |
| 2004/0167374 A1 | 8/2004 | Schweich |
| 2004/0167580 A1 | 8/2004 | Mann et al. |
| 2004/0225304 A1 | 11/2004 | Vidlund et al. |
| 2004/0267306 A1 | 12/2004 | Blaeser et al. |
| 2005/0065506 A1 | 3/2005 | Phan |
| 2005/0075723 A1 | 4/2005 | Schroeder et al. |
| 2005/0096498 A1 | 5/2005 | Houser et al. |
| 2005/0101984 A1* | 5/2005 | Chanduszko ...... A61B 17/0057 606/185 |
| 2005/0137688 A1 | 6/2005 | Salahieh et al. |
| 2005/0143620 A1 | 6/2005 | Mortier et al. |
| 2005/0149115 A1 | 7/2005 | Roue et al. |

(56) References Cited

U.S. PATENT DOCUMENTS

| | | |
|---|---|---|
| 2005/0192599 A1 | 9/2005 | Demarais |
| 2005/0215851 A1 | 9/2005 | Kim et al. |
| 2005/0288613 A1 | 12/2005 | Heil, Jr. |
| 2006/0004408 A1 | 1/2006 | Morris et al. |
| 2006/0079736 A1 | 4/2006 | Chin et al. |
| 2006/0131238 A1 | 6/2006 | Xu |
| 2006/0135962 A1 | 6/2006 | Kick et al. |
| 2006/0161040 A1 | 7/2006 | McCarthy et al. |
| 2006/0161238 A1 | 7/2006 | Hall |
| 2006/0167416 A1 | 7/2006 | Mathis et al. |
| 2006/0178550 A1 | 8/2006 | Jenson |
| 2006/0200002 A1 | 9/2006 | Guenst |
| 2006/0241340 A1 | 10/2006 | Schroeder et al. |
| 2006/0247672 A1 | 11/2006 | Vidlund et al. |
| 2006/0276684 A1 | 12/2006 | Speziali |
| 2007/0005018 A1 | 1/2007 | Tkebuchava |
| 2007/0010876 A1 | 1/2007 | Salahieh et al. |
| 2007/0049971 A1 | 3/2007 | Chin et al. |
| 2007/0055303 A1 | 3/2007 | Vidlund et al. |
| 2007/0073274 A1 | 3/2007 | Chin et al. |
| 2007/0112244 A1 | 5/2007 | McCarthy et al. |
| 2007/0112425 A1* | 5/2007 | Schaller ........... A61B 17/00234 623/2.37 |
| 2007/0161846 A1 | 7/2007 | Nikolic et al. |
| 2007/0203503 A1 | 8/2007 | Salahieh et al. |
| 2007/0265658 A1 | 11/2007 | Nelson et al. |
| 2007/0270751 A1* | 11/2007 | Stangenes ........ A61B 17/00234 604/164.1 |
| 2007/0287884 A1 | 12/2007 | Schena |
| 2008/0058650 A1 | 3/2008 | Saadat et al. |
| 2008/0082132 A1 | 4/2008 | Annest et al. |
| 2008/0097148 A1 | 4/2008 | Chin et al. |
| 2008/0234717 A1 | 9/2008 | Bruszewski |
| 2008/0269551 A1 | 10/2008 | Annest et al. |
| 2008/0294251 A1 | 11/2008 | Annest et al. |
| 2009/0093670 A1 | 4/2009 | Annest et al. |
| 2009/0270980 A1 | 10/2009 | Schroeder et al. |
| 2009/0287165 A1 | 11/2009 | Drapeau et al. |
| 2009/0287304 A1 | 11/2009 | Dahlgren et al. |
| 2010/0010538 A1 | 1/2010 | Juravic et al. |
| 2010/0016655 A1 | 1/2010 | Annest et al. |
| 2010/0057000 A1 | 3/2010 | Melsheimer et al. |
| 2010/0114140 A1 | 5/2010 | Chanduszko et al. |
| 2010/0268020 A1 | 10/2010 | Chin et al. |
| 2011/0160750 A1 | 6/2011 | Annest et al. |
| 2011/0264072 A1* | 10/2011 | Kunis ................ A61B 17/3478 604/506 |
| 2011/0270191 A1 | 11/2011 | Paul et al. |
| 2012/0190958 A1 | 7/2012 | Annest et al. |
| 2013/0090523 A1 | 4/2013 | Van Bladel et al. |
| 2013/0090672 A1 | 4/2013 | Butler et al. |
| 2013/0090684 A1 | 4/2013 | Van Bladel et al. |
| 2013/0096579 A1 | 4/2013 | Annest et al. |
| 2013/0324787 A1 | 12/2013 | Chin et al. |
| 2013/0325041 A1 | 12/2013 | Annest et al. |
| 2014/0031613 A1 | 1/2014 | Annest et al. |
| 2014/0051916 A1 | 2/2014 | Chin et al. |
| 2014/0330296 A1 | 11/2014 | Annest et al. |
| 2015/0066082 A1 | 3/2015 | Moshe et al. |
| 2015/0066139 A1 | 3/2015 | Bladel et al. |
| 2015/0238182 A1 | 8/2015 | Annest et al. |
| 2016/0022422 A1 | 1/2016 | Annest et al. |
| 2016/0030026 A1 | 2/2016 | Bladel et al. |
| 2016/0089132 A1 | 3/2016 | Butler et al. |
| 2016/0095600 A1 | 4/2016 | Annest et al. |
| 2016/0120648 A1 | 5/2016 | Chin et al. |
| 2016/0206427 A1 | 7/2016 | Annest et al. |

FOREIGN PATENT DOCUMENTS

| | | |
|---|---|---|
| WO | 2002/30335 A2 | 4/2002 |
| WO | 2003/032818 A3 | 4/2003 |
| WO | 2005/092203 A1 | 10/2005 |
| WO | 2006/044467 A2 | 4/2006 |
| WO | 2007/022519 A2 | 2/2007 |
| WO | 2004-043267 A2 | 5/2007 |
| WO | 2012-090206 A2 | 7/2012 |
| WO | 2013-049761 A1 | 4/2013 |

OTHER PUBLICATIONS

Extended European Examination Report of EP Patent Application 06802038.7 dated Nov. 12, 2013, 13 pages.
International Search Report and Written Opinion of PCT Application No. PCT/US06/22594, dated Oct. 1, 2008, 4 pages.
International Search Report and Written Opinion of PCT Application No. PCT/US06/32663, dated Jul. 31, 2007, 5 pages.
International Search Report and Written Opinion of PCT Application No. PCT/US08/64255, dated Sep. 29, 2008, 13 pages.
International Search Report and Written Opinion of PCT Application No. PCT/US08/78810, dated Feb. 12, 2009, 9 pages.
International Search Report and Written Opinion of PCT Application No. PCT/US09/51288, dated Sep. 15, 2009, 7 pages.
International Search Report and Written Opinion of PCT Application No. PCT/US12/58074, dated Mar. 13, 2013, 18 pages.
International Search Report and Written Opinion of PCT Application No. PCT/US2005/036690, dated Jul. 9, 2007, 6 pages.
International Search Report and Written Opinion of PCT/US2012/058106, dated Nov. 26, 2012, 14 pages.
International Search Report and Written Opinion of PCT/US2012/58176, dated Jan. 8, 2013, 19 pages.
International Search Report and Written Opinion of PCT/US2012/058182, dated Mar. 1, 2013, 19 pages.
International Report on Patentability of PCT/US2012/058074 dated Apr. 10, 2014, 8 pages.
International Report on Patentability of PCT/US2012/058176 dated Apr. 10, 2014, 11 pages.
Office Action of EP Patent Application 06802038.7 dated Sep. 11, 2014, 4 pages.
International Search Report and Written Opinion of PCT Application No. PCT/US2014/053209 dated Mar. 2, 2015, 18 pages.
USPTO—STIC Search Results—NPL (Dec. 11, 2014).
USPTO—STIC Search Results—PATENTS (Dec. 11, 2014).
European Examination Report of EP Patent Application 12837466.7 dated Jun. 6, 2016, 14 pages.
European Search Report dated Dec. 12, 2016 EP Patent Application No. 14800594.5, all pages.
International Search Report and Written Opinion of PCT/US2014/038834 dated Oct. 16, 2014, 16 pages.
International Report on Patentability of PCT/US2014/038834 dated Dec. 3, 2015, 11 pages.

* cited by examiner

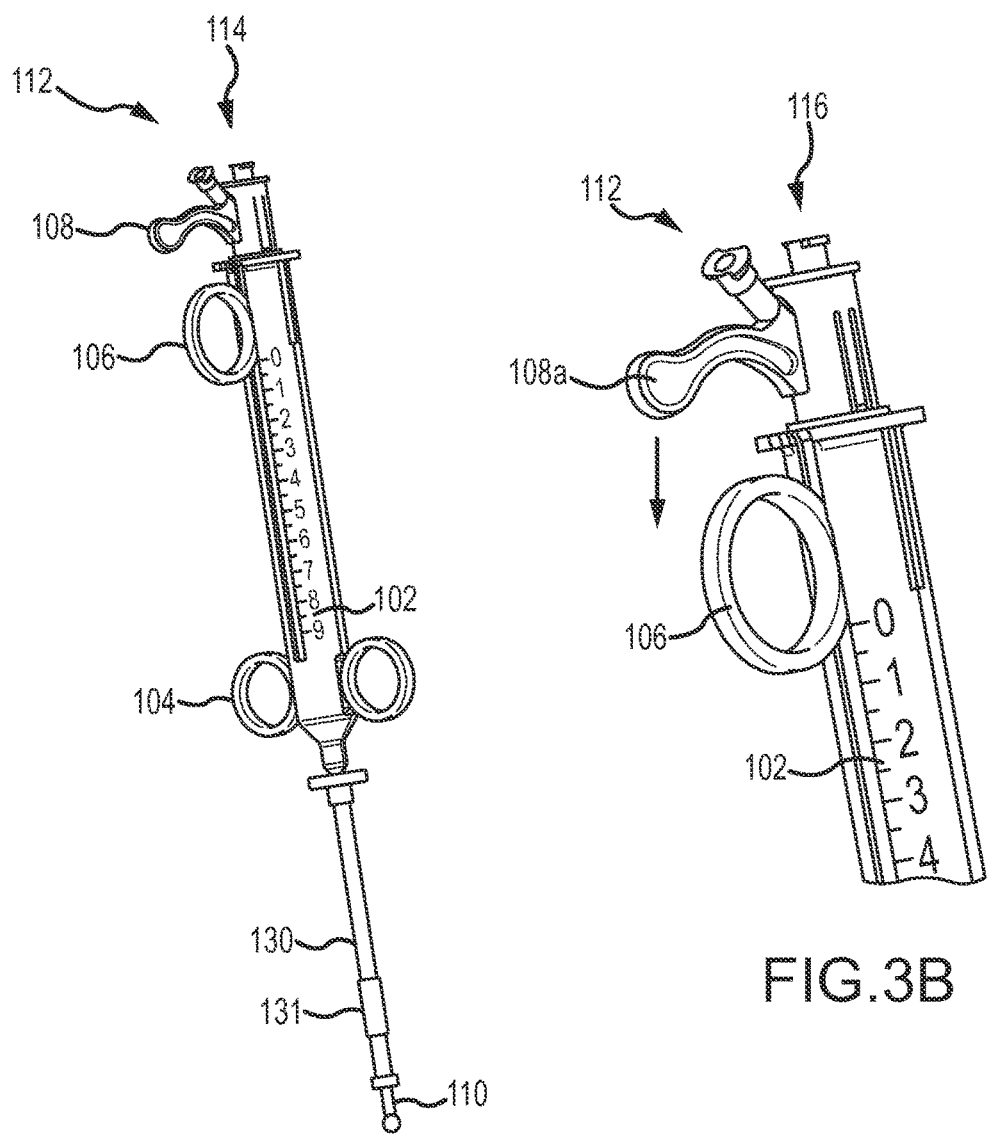
FIG.3A
FIG.3B
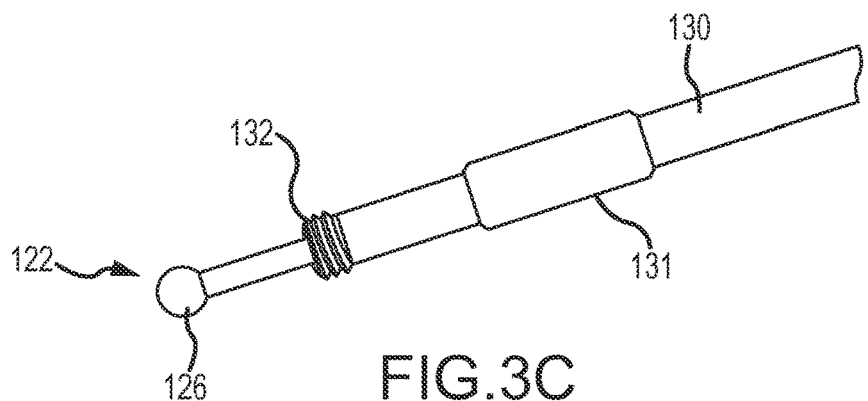
FIG.3C

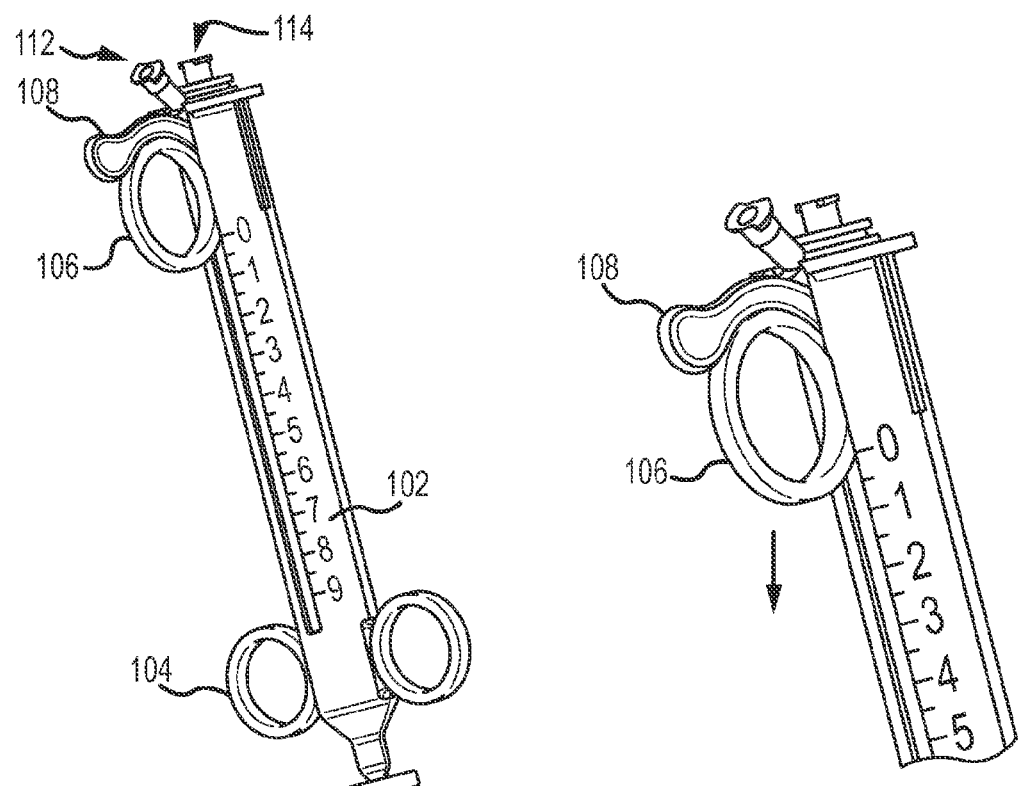
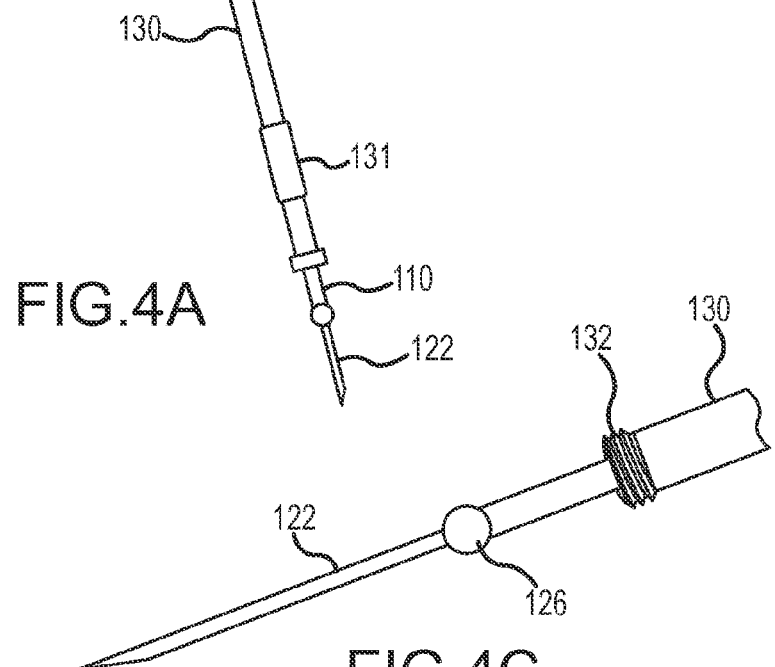
FIG.4A  FIG.4B  FIG.4C

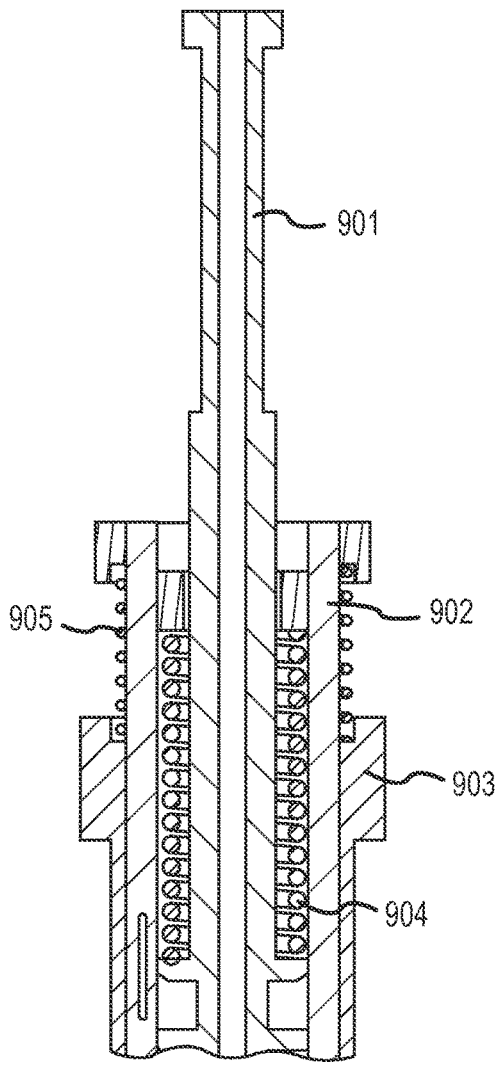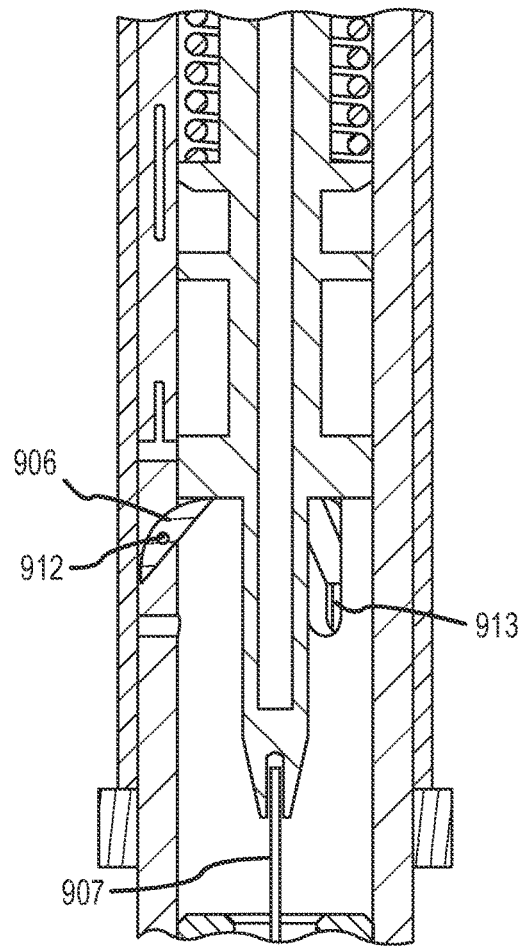
FIG.9B
FIG.9C

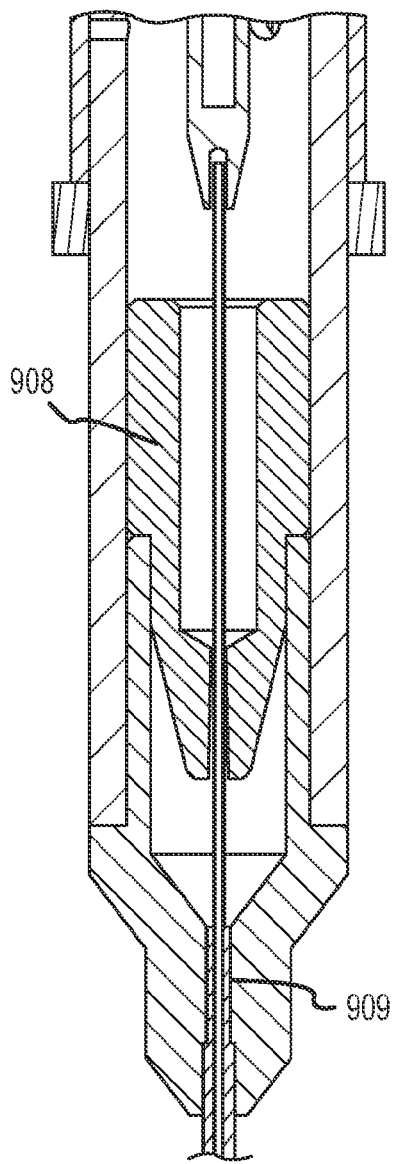
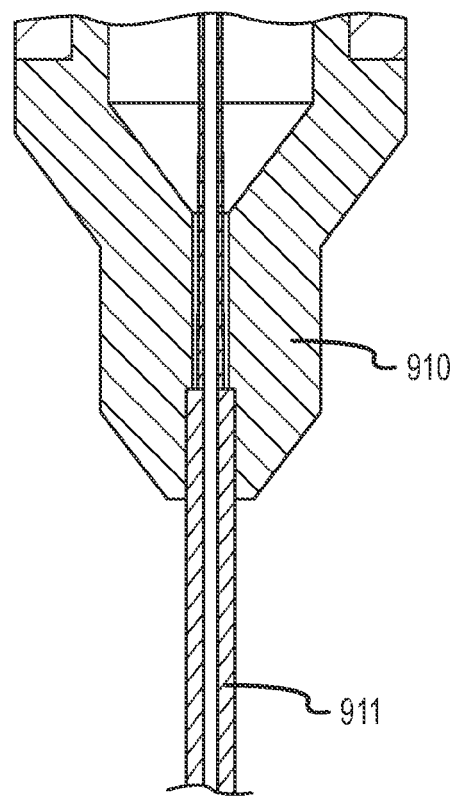
FIG.9D
FIG.9E

CARDIAC TISSUE PENETRATING DEVICES, METHODS, AND SYSTEMS FOR TREATMENT OF CONGESTIVE HEART FAILURE AND OTHER CONDITIONS

BACKGROUND OF THE INVENTION

The present invention is related to improved medical devices, systems, and methods, with many embodiments being particularly useful for reducing the distance between two points in tissue in a minimally or less invasive manner. Specific reference is made to the treatment of a failing heart, particularly the alleviation of congestive heart failure and other progressive heart diseases. The provided devices, systems, and methods will often be used to resize or alter the geometry of a ventricle in a failing heart, such as by reducing its radius of curvature through the process of excluding a portion of the circumference from contact with blood, and thereby reduce wall stress on the heart and improve the heart's pumping performance. Although specific reference is made to the treatment of congestive heart failure, embodiments of the present invention can also be used in other applications in which tissue geometry is altered.

Exemplary embodiments described herein provide implants and methods for alleviating congestive heart failure and other progressive diseases of the heart. Congestive heart failure may, for example, be treated using one or more implants which are selectively positioned relative to a first wall of the heart (typically an interventricular septum), and another wall of the heart so as to exclude scar tissue and limit a cross sectional area, or distance across a ventricle. Functional deterioration of the heart tissues may be inhibited by decreasing a size of the heart chamber and/or approximating tissues so that stress on the tissues is limited. Implant locations and overall chamber remodeling achieved by placement of a series of implants may be determined so as to provide a beneficial volumetric decrease and chamber shape.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunction due to degenerative processes or other causes, cardiomyopathy (a primary disease of the heart muscle itself), congenital heart defects, infections of the heart tissues, and the like. However, in many cases congestive heart failure may be triggered by a heart attack or myocardial infarction. Heart attacks can cause scar tissue that interferes with the heart muscle's healthy function, and that scar tissue can progressively replace more and more of the contractile heart tissue. More specifically, the presence of the scar may lead to a compensatory neuro-hormonal response by the remaining, non-infarcted myocardium leading to progressive dysfunction and worsening failure.

People with heart failure may have difficulty exerting themselves, often becoming short of breath, tired, and the like. As blood flow out of the heart decreases, pressure within the heart increases. Not only does overall body fluid volume increase, but higher intracardiac pressure inhibits blood return to the heart through the vascular system. The increased overall volume and higher intracardiac pressures result in congestion in the tissues. Edema or swelling may occur in the legs and ankles, as well as other parts of the body. Fluid may also collect in the lungs, interfering with breathing (especially when lying down). Congestive heart failure may also be associated with a decrease in the ability of the kidneys to remove sodium and water, and the fluid buildup may be sufficient to cause substantial weight gain. With progression of the disease, this destructive sequence of events can cause the progressive deterioration and eventual failure of the remaining functional heart muscle.

Treatments for congestive heart failure may involve rest, dietary changes, and modified daily activities. Various drugs may also be used to alleviate detrimental effects of congestive heart failure, such as by dilating expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may involve (for example) surgical left ventricular reconstruction, ventricular restoration, the Dor procedure, and the like. If the heart becomes sufficiently damaged, even more drastic surgery may be considered. For example, a heart transplant may be the most viable option for some patients. These surgical therapies can be at least partially effective, but typically involve substantial patient risk. While people with mild or moderate congestive heart failure may benefit from these known techniques to alleviate the symptoms and/or slow the progression of the disease, less traumatic, and therefore, less risky therapies which significantly improve the heart function and extend life of congestive heart failure patients has remained a goal.

It has been proposed that an insert or implant be used to reduce ventricular volume of patients with congestive heart failure. With congestive heart failure, the left ventricle often dilates or increases in size. This can result in a significant increase in wall tension and stress. With disease progression, the volume within the left ventricle gradually increases and blood flow gradually decreases, with scar tissue often taking up a greater and greater portion of the ventricle wall. By implanting a device which brings opposed walls of the ventricle into contact with one another, a portion of the ventricle may be excluded or closed off. By reducing the overall size of the ventricle, particularly by reducing the portion of the functioning ventricle chamber defined by scar tissue, the heart function may be significantly increased and the effects of disease progression at least temporarily reversed, halted, and/or slowed.

BRIEF SUMMARY OF THE INVENTION

The present invention generally provides improved medical devices, systems, and methods. Exemplary embodiments of the devices are described for use in reducing the distance between a region along the septum and a region of an external wall of the left ventricle of a heart in a less or minimally invasive manner. According to one embodiment, a tissue penetrating device is provided. The tissue penetrating device includes an elongate shaft having a proximal end, a distal end, a lumen extending between the proximal end and a distal end. The proximal end may be positioned outside a patient's body while the distal end is positioned within the patient's body, such as adjacent an organ (e.g., a heart) or tissue of the patient. The tissue penetrating device also includes a first needle disposed within the lumen of the elongate shaft. The first needle is extendable distally of the elongate shaft's distal end between a first configuration and a second configuration. The first needle has a proximal end, a distal end, and a lumen extending between the proximal end and a distal end. In the first configuration, the needle is disposed within the elongate shaft's lumen and is substantially aligned with an axis of the elongate shaft's lumen. In the second configuration, the first needle is extended distally of the elongate shaft's distal end and bends or curves away from the axis of the elongate shaft's lumen. The tissue penetrating device further includes a second needle that is disposed within the first needle's lumen. The second needle is extendable distally from the distal end of the first needle when the first needle is positioned in the first configuration and is also extendable distally from the distal end of the first needle when the first needle is positioned in the second configuration. The second needle may be extended distally from the first needle to penetrate tissue of the patient, such as a wall of a heart or other organ.

In some embodiments, the second needle may have a proximal end, a distal end, and a lumen extending between the proximal end and a distal end. In such embodiments, a guidewire may be inserted through the lumen of the second needle and into the patient's body, such as into a chamber of the patient's heart. In some embodiments, the second needle may be configured to measure or monitor fluid pressure within the patient's body. The fluid pressure may be measured or monitored to determine a location within a heart chamber of the patient (e.g., measure or monitor left ventricle heart pressure, right ventricle heart pressure, and/or damped pressure due to the needle being imbedded within the tissue walls of the heart).

In some embodiments, the tissue penetrating device may additionally include a tool body that is positioned at the proximal end of the elongate shaft. The tool body may be configured to be grasped by a physician to enable the physician to extend the first needle and the second needle so as to penetrate the patient's tissue. The tool body may include a first trigger member or mechanism that is slidable axially along the tool body to extend and retract the first needle relative to the elongate shaft's distal end. The tool body may also include a second trigger member or mechanism that is operable independently of the first trigger member or mechanism. The second trigger member or mechanism may be slidable axially along the tool body to extend and retract the second needle relative to the first needle. In some embodiments, the elongate shaft may be a catheter device.

In some embodiments, the tool body may include a spring trigger mechanism that causes the first needle and/or the second needle to rapidly deploy distally upon actuation of the spring trigger mechanism. In some embodiments, the distal end of the elongate shaft may include a locking mechanism that is couplable with an attachment or tissue anchoring device that may be removably attached to the patient's tissue or organ (e.g., the heart). In some embodiments, when in the second configuration, the first needle may bend or curve away from the axis of the elongate shaft's lumen by between about 45 and 210°. In other embodiments, the first needle may bend or curve away from the axis of the elongate shaft's lumen by between about 80 and 90°. In some embodiments, the distal end of the first needle and/or second needle may include a fluid pathway that allows the user to monitor or measure pressure within the patient's body, such as within a chamber of the heart. Monitoring or measuring pressure may allow the location of the tip of the needle to be determined. For example, left ventricle heart pressure may be monitored or measured, right ventricle heart pressure may be monitored or measured, and/or a damped pressure may be monitored or measured when the needle is imbedded within the wall of the heart (e.g., septum wall).

This may allow a physician to determine that the needle tip is near or within the corresponding heart chamber or within heart tissue. In some embodiments, the distal end of the first needle and/or second needle may include a pressure transducer that may be used to sense pressure in or around the patient's tissue or organ, such as in or around the heart as described above.

According to another embodiment, a method of penetrating tissue of a patient is provided. The method includes providing a tissue penetrating device, where the tissue penetrating device includes: an elongate shaft having a proximal end, a distal end, and a lumen extending between the proximal end and a distal end; a first needle disposed within the lumen of the elongate shaft and extendable distally of the elongate shaft's distal end between a first configuration and a second configuration, the first needle having a proximal end, a distal end, and a lumen extending between the proximal end and a distal end; and a second needle disposed within the first needle's lumen and extendable therefrom. The method also includes advancing the first needle distally of the elongate shaft's distal end so as to position the first needle's distal end adjacent the patient's tissue. The first needle may bend or curve away from an axis of the elongate shaft's lumen as the first needle extends distally of the elongate shaft's distal end. The method further includes advancing the second needle distally of the first needle's distal end so as to penetrate the patient's tissue with the second needle.

In some embodiments, the second needle may include a proximal end, a distal end, and a lumen extending between the proximal end and a distal end. In such embodiments, the method may further include inserting a guidewire through the lumen of the second needle and into the patient's body. In some embodiments, advancing the first needle may include actuating a first trigger mechanism of a tool body, where the tool body is positioned at a proximal end of the elongate shaft and is configured to be operated by a physician. In some embodiments, advancing the second needle may include actuating a second trigger mechanism of the tool body. The second trigger mechanism may be operable independently of the first trigger mechanism. In some embodiments, the first trigger mechanism and/or the second trigger mechanism may include a spring trigger mechanism that causes the first needle and/or the second needle to rapidly deploy upon actuation of the spring trigger mechanism. In other embodiments, advancing the first needle and/or second needle may include actuating a trigger mechanism that causes the first needle to be pneumatically advanced via pressurized fluids. In some embodiments, the elongate shaft may be a catheter device.

According to another embodiment, a method of penetrating cardiac tissue for treatment of congestive heart failure is provided. The method includes positioning a proximal end of the elongate shaft adjacent an external wall of the patient's heart. A distal end of the elongate shaft may be positioned outside of the patient's body. The method also includes advancing a needle distally of a distal end of the elongate shaft and through the external wall, where the needle is disposed centrally within a lumen of the elongate shaft. The method further includes advancing a sleeve, or outer needle, over the needle and through the external wall, where the sleeve is disposed within the lumen of the elongate shaft and is coaxially aligned with the needle. The method additionally includes advancing the sleeve distally of the external wall to position the sleeve and needle adjacent the septal wall of the patient's heart. As the sleeve is advanced distally of the external wall, the sleeve may curve or bend away from an axis of the elongate shaft's lumen. The method may additionally include advancing the needle distally of the distal end of the sleeve and through the septal wall of the patient's heart.

In some embodiments, the guidewire may be inserted through a lumen of the needle and through the external wall and septal wall so that the guidewire is positioned within a chamber of the heart. The guidewire may be joined with a snare that has been inserted within the chamber of the heart along a different path than that of the guidewire. Joining the guidewire and the snare may couple the paths of the guidewire and the snare. The method may additionally include advancing a first anchor and an elongate tension member into the chamber along the joined paths of the guidewire and snare. The first anchor may be positioned distally of the septal wall and the tension member may extend from the septal wall, through the external wall and septal wall, and outside the patient's body.

The method may additionally include coupling a second anchor (e.g., an epicardial anchor) to the tension member, advancing the second anchor along the tension member to a position proximate the external wall, and applying tension between the first anchor and the second anchor so that the anchors urge the septal wall and external wall to engage. In some embodiments, the sleeve may be an outer needle that is slidable over the needle and disposed within the elongate shaft's lumen. In some embodiments, the method may additionally include sensing a pressure with a distal end of the needle and/or sleeve via a fluid pathway of the needle and/or sleeve, or via a pressure transducer of the needle and/or sleeve. In some embodiments, the elongate shaft may be a catheter device.

According to another embodiment, a method of penetrating tissue of a patient is provided. The method includes positioning a proximal end of an elongate shaft adjacent tissue of a patient (e.g., an external wall of the patient's heart). The method also includes advancing a needle distally of a distal end of the elongate shaft and through the tissue. Prior to advancement of the needle, the needle may be disposed centrally within a lumen of the elongate shaft and an axis of a distal tip of the needle may be substantially aligned with an axis of the lumen. The method further includes advancing the distal tip of the needle distally of the tissue to position the distal tip adjacent additional tissue of the patient (e.g., a septal wall of the patient's heart). The method additionally includes causing the needle to be flexed as the needle is advanced distally of the tissue so that the axis of the distal tip of the needle bends or curves away from the axis of the lumen. The method additionally includes advancing the needle through the additional tissue of the patient (e.g., through the septal wall).

BRIEF DESCRIPTION OF THE DRAWINGS

The present invention is described in conjunction with the appended figures:

FIGS. 3A-3C illustrate the tissue penetrating device of FIG. 1 with an inner and outer needle retracted within an elongate shaft according to an embodiment.

FIGS. 4A-4C illustrate the tissue penetrating device of FIG. 1 with the inner needle extending from the elongate shaft according to an embodiment.

FIGS. 9B-E illustrate enlarge cross section views of the tissue penetrating device of FIG. 9A.

Figure 1:
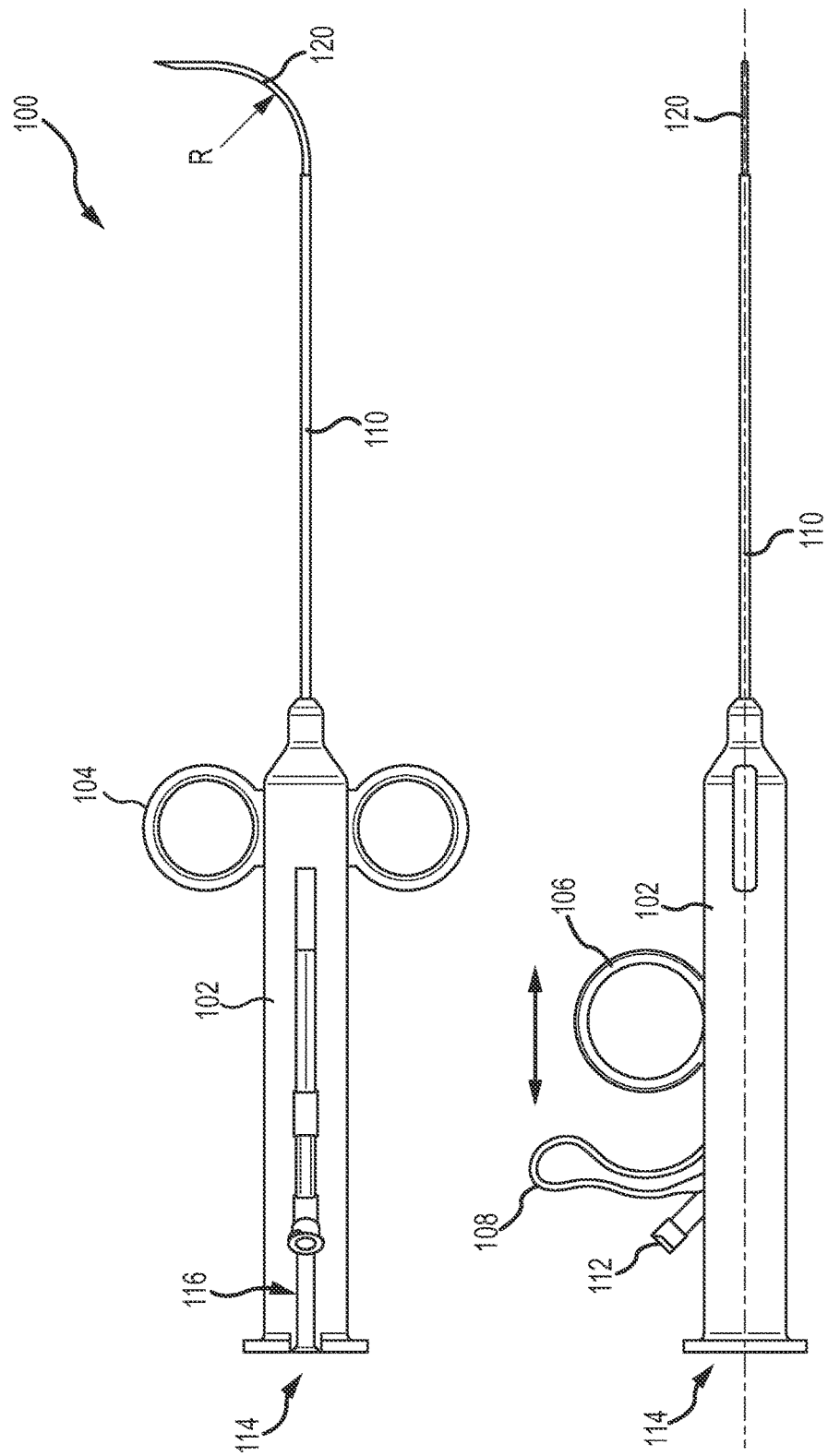
FIG. 1 illustrates a front and side view of a tissue penetrating device according to an embodiment.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

The present invention generally provides improved medical devices, systems, and methods. Exemplary embodiments of the devices are described for use in reducing the distance between a region along the septum and a region of an external wall of the left ventricle of a heart in a less or minimally invasive manner. Hence, embodiments of the tools and methods described herein may find specific use in the treatment of congestive heart failure and other progressive heart diseases by reconfiguring abnormal heart geometry that may be contributing to heart dysfunction. For congestive heart failure therapies, perforating both the exterior wall and the septum from an epicardial approach can provide significant benefits in control over the locations of implant deployments, thereby effectively enhancing the resulting reshaping of the ventricular chamber. Despite this largely epicardial approach, there are surprising benefits to guiding deployment of the implant from along both the epicardial access path and another access path into and via an access path through the right ventricle. This additional right atrial access path into the heart may be via the superior vena cava, the inferior vena cava, the right atrial appendage, or the like, and the pathways may be joined together by coupling of a snare to a guidewire or the like within the right ventricle, the right atrium, the right pulmonary artery, or the like. While a variety of tools will be described herein for providing access pathways, for joining pathways together within the heart, for deploying implants, for maintaining hemostasis, and the like, it should be recognized that alternative embodiments may employ additional or alternative structures, some of which may be off-the-shelf, and some of which may be new structures configured particularly for use in the advantageous therapies described herein.

Joining pathways may be accomplished by using a guidewire and snare device. To join the pathways, the guidewire is often inserted through the external wall and septal wall of the heart. The external wall and/or septal wall are often composed of relatively tough scar tissue, which makes insertion of the guidewire through these walls relatively challenging. For example, relatively thin and long needles (e.g., 17 Gauge (0.058″)) are often used to penetrate the scar tissue of the external and/or septal walls. The needles need to be relatively long to allow a physician to position the needle through a small incision, through the external wall, and through the septal wall. These thin and long needles often bend or buckle as they are pressed firmly against the tough scar tissue, which complicates the wall penetrating processes. Further, the needle insertion locations for the external wall and septal wall are typically not aligned relatively to one another. Rather, the insertion locations are often angled or offset from one another by some degree. As such, straight needles are often relatively difficult to maneuver and/or work with in penetrating both the external wall and the septal wall.

The tissue penetrating devices described herein are able to easily penetrate tough scar tissue while compensating for the offset insertion locations of the external and septal wall. This is accomplished by providing a needle and sleeve combination, or a pair of needles, that are coaxially aligned and that slide relative to one another. The needle (hereinafter inner needle) is a small sharp needle that is used to initially penetrate the tough scare tissue of the external wall and septal wall. In initially penetrating the scar tissue, a sleeve or outer needle (hereinafter outer needle) is positioned adjacent the scar tissue and over the inner needle. In this manner the outer needle supports the inner needle and prevents or reduces bending and/or buckling of the inner needle during insertion of the inner needle through the tough scar tissue. After the inner needle penetrates the scar tissue, the outer needle may then be advanced over the inner needle and through the tough scar tissue of the external wall or septal wall.

The outer needle may be made of a flexible shape-memory material, such as nitinol, that is able to bend or flex as the outer needle is advanced distally of a distal end of a surgical device's an elongate shaft. The flexible shape-memory material allows the outer needle to bend away from the insertion location of the external wall and toward the insertion location of the septal wall after the outer needle is inserted through and advanced distally of the external wall. In this manner, the inner needle may be positioned adjacent and used to penetrate through the offset insertion locations of the external wall and septal wall. The outer needle may be configured to have any desired degree of bend so as to accommodate patients of various shape and size. The inner needle may likewise be made of a flexible material, such as nitinol, to allow the inner needle to be advanced within a lumen of the outer needle without significantly altering the bend or flexed configuration of the outer needle. The outer and inner needle may be positioned adjacent a desired insertion point on the septal wall and the inner needle may be advanced distally of the outer needle and through the septal wall. A guidewire may then be inserted through a lumen of the inner needle, through the external wall and septal wall, and into a chamber of the heart for snaring and joining insertion paths as described herein.

For convenience in describing the embodiments herein, the sleeve or outer component is referred to herein as an "outer needle." It should be realized, however, that the outer component is not limited to needles and that other types of component may be used, such as: a sleeve, catheter, elongate shaft, or tube that is configured to track over the inner needle and bend or flex as described herein. In some embodiments, however, the outer component may be a needle that is capable to some degree of insertion through tissue with or without the assistance of the inner needle. Having generally described some embodiments, additional feature of the embodiments will be recognized with reference to the figures described below.

Referring now to FIG. 1, illustrated is a tissue penetrating device 100 that may be used to penetrate various tissue of the patient, such as an external wall and/or septal wall of a heart. Tissue penetrating device 100 includes a tool body 102 that may be grasped by a physician during a tissue penetrating operation. Attached to body 102 is a pair of finger guides 104 through which the physician may insert his or her fingers. A second finger guide 106, or trigger mechanism, is also slidably coupled with body 102. Finger guide 106 is able to slide axially along body 102 via track 116 to deploy and retract an outer needle 120 relative to an elongate shaft 110 of device 100. A second trigger mechanism 108 is also slidably coupled with body 102. Second trigger mechanism 108 is axially movable along body 102 via track 116 to deploy and retract an inner needle (122 of FIG. 2 and the like) relative to elongate shaft 110 and outer needle 120.

Second trigger mechanism 108 is typically operable independently of first trigger mechanism 106 so that the inner needle 122 and outer needle 120 are independently deployable and retractable to at least some degree relative to one another. Body 102 also includes one or more ports, 112 and 114, through which a guidewire, tether or tension member, and the like may be inserted; or which may function to fluidly couple a pressure sensing fluid pathway with an external pressure monitoring or measuring device (not shown).

Outer needle 120 and inner needle 122 are disposed within a lumen of the elongate shaft 110 and are slidable relative thereto so as to be extendable from and retractable within the lumen of elongate shaft 110. Further, outer needle 120 and the inner needle 122 are coaxially aligned and slidable relative to one another. Outer needle 120 is disposed over inner needle 122 with inner needle 122 being slidably disposed within a lumen of outer needle 120. Inner needle 122 is extendable distally beyond a distal end of outer needle 120 and retractable within the lumen of outer needle 120.

Figure 2:
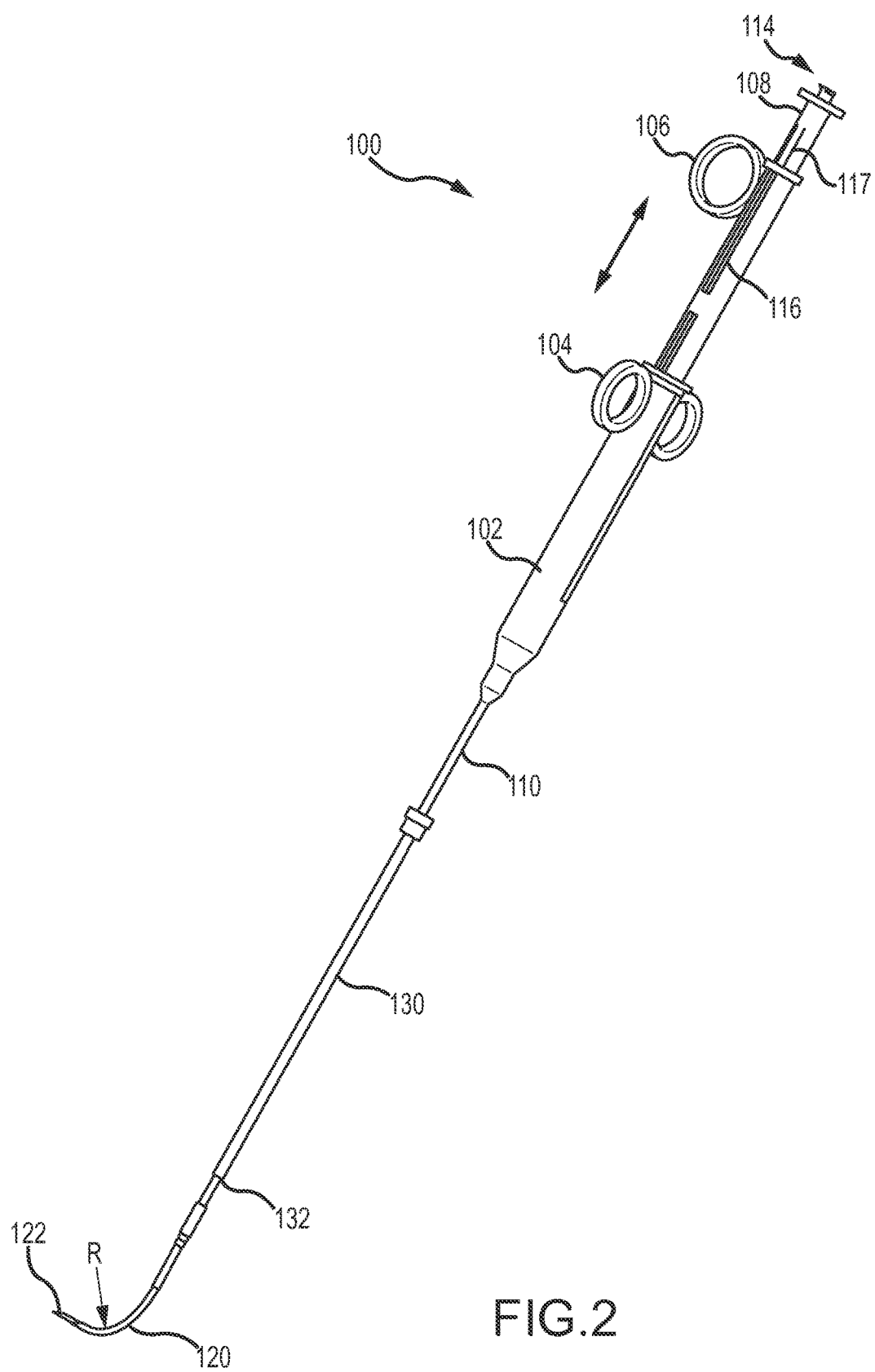
FIG. 2 illustrates a perspective view of the tissue penetrating device of FIG. 1.

FIG. 2 shows a perspective view of another embodiment of tissue penetrating device 100. FIG. 2 illustrates the finger guides 104 positioned at a proximal end of body 102. FIG. 2 further illustrates the second finger guide 106 slid proximally away from finger guides 104, which typically results in outer needle 120 and inner needle 122 being retracted within the lumen of elongate shaft 110. For illustrative purposes, however, outer needle 120 is shown being extended distally of elongate shaft 110 even though the second finger guide 106 is slid proximally away from finger guides 104. FIG. 2 additionally shows that the second trigger mechanism 108 may be coupled with a shaft or tube that is slidable within body 102 and/or within a shaft or tube of first trigger mechanism 106. The shaft or tube of the second trigger mechanism 108 and/or the shaft or tube of the first trigger mechanism 106 may include locking components 117 that help maintain the position of the second trigger mechanism's shaft or tube and/or first trigger mechanism's shaft or tube relative to one another and/or to body 102. In some embodiments, the locking component 117 may help maintain a positional relationship between the inner needle 122 and the outer needle 120. For example, as the outer needle 120 is advanced distally of the distal end of elongate shaft 110, the inner needle 122 may remain in position until the distal tips of both the inner needle 122 and the outer needle 120 substantially align. Afterward, the locking component 117 may lock the first and second trigger mechanisms, 106 and 108, together so that further advancement of the outer needle 120 causes the inner needle 122 to also advance.

FIG. 2 additionally shows that an outer sleeve 130 may be slidably disposed over elongate shaft 110. Outer sleeve 130 may include a locking mechanism 132 that is couplable with a tissue anchoring device (not shown) that is positioned adjacent and/or removably coupled with tissue or an organ of the body (e.g., the heart) through which the inner needle 122 and/or outer needle 120 are to be inserted. As shown in FIGS. 1 and 2, when axially extended from the elongate shaft 110, the outer needle 120 bends, flexes, or curves away from an axis of the elongate shaft 110's lumen. As described herein, outer needle 120 may be made of a flexible shape-memory material, such as nitinol, that is configured to automatically bend or curve by a radius R as the outer needle 120 is advanced distally of a distal end of an elongate shaft 110. The flexible material of outer needle 120 also allows the outer needle to straighten when the outer needle 120 is refracted within the elongate shaft 110's lumen. When retracted within elongate shaft 110's lumen, outer needle 120 is substantially aligned with the axis of elongate shaft 110's lumen. The radius of curvature R may be selected such that when the outer needle 120 is advanced distally from a distal end of elongate shaft 110, a distal end of outer needle 120 is curved or bent away from the axis of the elongate shaft 110's lumen by between 45 and 210 degrees, and more commonly by about 80 and 120 degrees, so as to enable the distal end of outer needle 120 and/or inner needle 122 to be positioned at offset insertion locations of the external and septal walls. In one embodiment, the radius of curvature R may be between about 10 and 38 mm. This radius of curvature range of outer needle 120 is found to be sufficient for the majority of patients.

In some embodiments, the radius of curvature R and/or degree of bend of the outer needle 120 may be dynamically adjusted. For example, when the outer needle 120 is made of nitinol, the radius of curvature R and/or bend of the outer needle 120 may be adjusted by varying the temperature of the needle. The temperature of the nitinol needle may be varied while the needle is within, or external to, the patient's body. The temperature of the nitinol needle may be varied automatically (e.g., by the patient's body temperature) or in a controlled manner (e.g., via resistive heating of the needle and the like). This variation and control of the outer needle 120's shape may allow a physician to adjust the needle to fit or conform to a specific patient's geometry and/or allow a single needle to be used in multiple instances, such as to place multiple anchors when treating congestive heart failure.

The inner needle 122 is similarly made of a flexible material, such as nitinol, that allows the inner needle 122 to curve, flex, or bend by radius R as the inner needle 122 is advanced simultaneously with outer needle 120, or slid within the lumen of outer needle 120. The flexibility of the inner needle 122 prevents the inner needle 122 from significantly straightening or otherwise affecting the radius of curvature R of outer needle 120. Stated differently, because the inner needle 122 is also made of a flexible material, the inner needle 122 may be advanced simultaneously with outer needle 120, or slid within the lumen of outer needle 120, and bent, flexed, or forced to curve by the outer needle 120 as the outer needle 120 is advanced distally from elongate shaft 110. As described herein, the inner needle does not significantly straighten or otherwise affect the radius of curvature R of the outer needle. It should be realized that some straightening or change in the radius of curvature R may occur, but that any such change is slight and not significant enough to greatly affect the positioning of the outer and inner needle relative to the heart. The flexibility of inner needle 122 also allows the inner needle 120 to be straightened when the inner needle 122 and/or outer needle 120 are retracted within elongate shaft 110's lumen. When retracted within the lumen of elongate shaft 110, inner needle 122 is substantially aligned with the axis of the elongate shaft 110's lumen.

The dual needle arrangement of the tissue penetrating device 100 stabilizes the inner needle 122 as the inner needle 122 is inserted through bodily tissue of the patient. Since both the inner needle 122 and the outer needle 120, which is coaxially aligned with and positioned over inner needle 122, are positioned adjacent the patient's tissue that is to be penetrated with inner needle 122, the outer needle 120 provides a relatively rigid sheath that reinforces the inner needle 122 as the inner needle is penetrated through the patient's tissue. This configuration prevents or reduces buckling or bending of the inner needle 122 as the inner needle 122 is inserted through the patient's tissue. This configuration also allows the penetrating force of the inner needle 122 to be concentrated at a distal tip of the inner needle 122, thereby enabling the inner needle 122 to easily puncture through tough scar tissue or other tissue, which may otherwise cause bending or buckling of the inner needle 122.

Although not shown in FIGS. 1 and 2, in some embodiments the first trigger mechanism 106 and/or second trigger mechanism 108 may be spring-loaded such that actuation of the first trigger mechanism 106 and/or second trigger mechanism 108 causes a spring to rapidly fire or deploy the outer needle 120 and/or inner needle 122 across the tissue of the patient (see FIGS. 9A-E). Spring-loading the first trigger mechanism 106 and/or second trigger mechanism 108 may allow the inner needle 122 and/or outer needle 120 to easily penetrate relatively tough scar tissue or other tissue. Spring-loading of the trigger mechanisms, however, is typically not necessary and in fact may not be desired, since the support provided by the outer needle 120 allows the inner needle 122 to easily penetrate tough scar tissue and other tissue. In other embodiments, the first and/or second trigger mechanism may include a pneumatic mechanism that causes the inner needle 122 and/or outer needle 120 to be advanced via pressurized fluids.

In some embodiments, inner needle 122 may be an approximately a 21 Gauge (0.033 in) needle while outer needle 120 is a slightly larger needle, such as a 17.5 Gauge (0.054 in) needle and the like. The dimensions of the needles may be adjusted based on need, patient size, application, procedure, or as otherwise desired. In some embodiments, an outer diameter of elongate shaft 110 and/or outer sleeve 130 is smaller than about 5 mm or 7.5 mm to allow the elongate shaft 110 and/or outer sleeve 130 to be inserted through a 5 mm or 7.5 mm trocar that is positioned through a relatively small incision in the patient's skin.

In some embodiments, the distal end of elongate shaft 110 may include a joint member (see 126 of FIG. 3C and the like) that is couplable with a tissue anchoring or attachment device (not shown) that is positioned on or adjacent tissue to be penetrated with inner needle 122. The joint member 126 may allow the elongate shaft 110 and body 102 to be aligned relative to the tissue anchoring device by some degree, such as up to between about 10 and 30 degrees. This allows the distal tip of elongate shaft 110 to be positioned adjacent the tissue to be penetrated with inner needle 122 and for the tissue penetrating device 100 to be offset so that the inner needle 122 will penetrate the tissue at a desired angle and/or so that the outer needle 120 will be positioned adjacent a desired insertion location of additional tissue after the outer needle 120 is advanced from elongate shaft 110 and flexed or curved by radius R. The joint member 126 allows the outer needle 120 and inner needle 120 to be steered posterior or anterior to the heart, or some feature of the heart. For example, the alignment of the elongate shaft 110 relative to the tissue anchoring device and heart may be adjusted so that a tip of the outer needle 120 (i.e., in a bent or straight configuration) and/or the inner needle 122 may be positioned closer to a heart's apex, base, valve, septal or exterior wall, and the like as desired. This effectively allows the outer and/or inner needle's tip to be steered within or relative to a patient's heart or other tissue as needed or desired, which facilitates in precise placement and/or penetration of the needles relative to the tissue. Steering of the outer needle 120 and/or inner needle 122 may be further facilitated via the use of an imaging device (e.g., a thoracoscope, fluoroscope, and the like).

In one embodiment, when the tissue penetrating device 100 is used for treating congestive heart failure, the tissue penetrating device 100 may be aligned so that the distal tip of elongate shaft 110 and/or outer needle 120 is positioned toward an apex of the heart, toward a base of the heart, and/or toward any other desired feature of the heart. In some embodiments, the distal tip of outer needle 120 and/or inner needle 122 may be radiopaque so that the distal tip is easily identifiable via an imaging device (e.g., a thoracoscope, fluoroscope, and the like). Further, the locking mechanism 132 of outer sleeve 130 may couple the elongate shaft 110 with the tissue anchoring device and the joint member 126 may allow some degree off-axis of the elongate shaft 110 relative to the tissue anchoring device.

In still other embodiments, the distal tip of the outer needle 120 and/or inner needle 122 may include a fluid pathway that allows a physician to monitor or measure pressure within the patient's body, such as within a chamber of the heart. Monitoring or measuring pressure may allow the location of the tip of the needle within the patient's body to be determined. In other embodiments, the distal tip of the needle 120 and/or inner needle 122 may include a pressure transducer that allows a pressure within the patient to be measured or determined as either or both needles are inserted through tissue of the patient and/or within one or more chambers within the body. For ease in describing the embodiments herein, the needle's pressure sensing fluid pathway, pressure transducer, and the like, will be referred to hereinafter as a pressure sensing element.

In one embodiment, when the tissue penetrating device 100 is used for treating congestive heart failure, the pressure sensing element (e.g., fluid pathway and the like) may be used to determine when the inner needle 122 and/or outer needle 120 have penetrated through the external wall of the heart, when the inner needle 122 and/or outer needle 120 are positioned within a chamber of the heart, when the inner needle 122 and/or outer needle 120 are positioned adjacent a septal wall of the heart, and/or when the inner needle 122 has penetrated through the septal wall and is positioned within the right ventricle of the heart. For example, the pressure sensing element may be used to measure or monitor left ventricle heart pressure, right ventricle heart pressure, and/or a damped pressure that corresponds to when the needle is imbedded within the wall of the heart (e.g., septum wall). The pressure sensing element may also be used to determine when the inner needle 122 and/or outer needle 120 are positioned adjacent scar tissue or contractile tissue of the heart to enable the physician to determine if the inner needle 122 and/or outer needle are adjacent a desired insertion point. In a specific embodiment, the inner needle 122 includes the pressure sensing element and the inner needle is used to sense pressure within the heart and/or elsewhere within the patient's body.

Referring now to FIGS. 3A-6B, illustrated is an embodiment of the operation of a tissue penetrating device 100. Specifically, FIGS. 3A-3C illustrate the first trigger mechanism 106 and the second trigger mechanism 108 being positioned in a proximal position relative to body 102 such that the inner needle 122 and outer needle 120 are fully retracted and disposed within the lumen of elongate shaft 110. As shown in FIG. 3C, a distal tip of the inner needle 122 may be positioned adjacent a distal tip of elongate shaft 110, or axially extend partially therefrom. FIG. 3C also illustrates the outer sleeve 130, locking mechanism 132, and joint member 126 in greater detail.

FIGS. 3A-3C further illustrate an alignment sleeve 131 that may be positioned near the distal end of outer sleeve 130 to coaxially align the outer sleeve 130 with a trocar or access tube that is positioned within the patient's body. As is known in the art, a trocar or access tube may be inserted within a small incision within the body, often between two ribs, and used as a port for inserting and removing catheters and/or other surgical devices from the body. Alignment sleeve 131 aligns the outer sleeve 130 within such a trocar or access tube to enable easy coupling of the locking mechanism 132 within a tissue anchoring device (not shown) that is positioned adjacent the heart or other organs. In some embodiments, alignment sleeve 131 is slidable about outer sleeve 130, while in other embodiments, alignment sleeve 131 is relatively fixed about outer sleeve 130. In some embodiments, locking mechanism 132 may comprise threads that may be threaded with a corresponding aperture of the tissue anchoring device. FIG. 3B illustrates an enlarged perspective view of body 102 and several components of the device 100 and illustrates that body 102 may include indicia that facilitates in informing a physician of the deployment of the outer needle 120 and/or inner needle 122.

With the inner needle 122 and outer needle 120 fully retracted and disposed within the lumen of elongate shaft 110, the distal tip of elongate shaft 110 may be positioned adjacent the patient's tissue to be penetrated with inner needle 122, and/or the distal tip of elongate shaft 110 may be coupled with a tissue anchoring device (not shown) that is positioned adjacent the patient's tissue. After the distal tip of elongate shaft 110 is positioned adjacent the patient's tissue, second trigger mechanism 108 may be slid distally along body 102 to axially advance inner needle 122 from the lumen of elongate shaft 110 and outer needle 120. The second trigger mechanism 108 may be slid distally along body 102 by placing a finger (e.g., a forefinger) within the first trigger mechanism 106 and by pressing on the second trigger mechanism 108 with another finger (e.g., a thumb). FIGS. 4A-4C illustrate the inner needle 122 extended from elongate shaft 110 after the second trigger mechanism 108 is slid distally along body 102. As shown in FIG. 4A, second trigger mechanism 108 is positioned directly adjacent the first trigger mechanism 106 after second trigger mechanism 108 is slid distally along body 102.

Figures 5A, 5B, 5C:
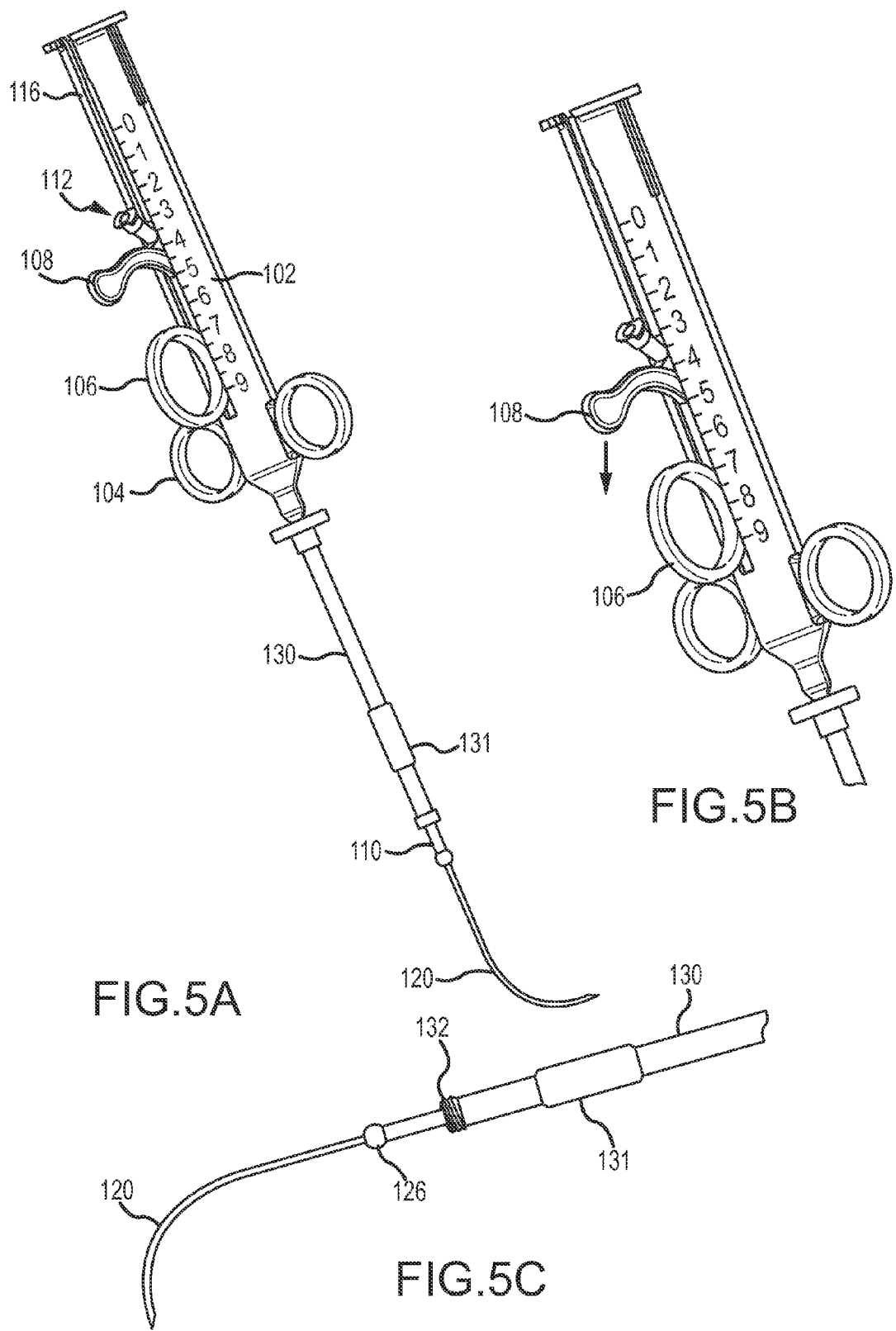
FIGS. 5A-5C illustrate the tissue penetrating device of FIG. 1 with the outer needle extending from the elongate shaft according to an embodiment.

Advancing the inner needle 122 from elongate shaft 110 as shown in FIG. 4C causes the inner needle 122 to penetrate through tissue positioned adjacent the distal tip of elongate shaft 110. In this configuration, first trigger mechanism 106 may be slid distally along body 102 to cause the outer needle 120 to slide within the lumen of elongate shaft 110 and advance distally from elongate shaft 110. Sliding the first trigger mechanism 106 distally along body 102 may be performed by placing a finger or fingers within finger guides 104 and by pressing on first trigger mechanism 106 with another finger. FIGS. 5A-5C illustrate the outer needle 120 extending from the distal end of elongate shaft 110 after the first trigger mechanism 106 is slid distally along body 102.

As shown, the inner needle 122 may be retracted within an outer needle 120 as the first trigger mechanism 106 is slid distally along body 102. Retraction of the inner needle 122 may occur automatically as the first trigger mechanism 106 is slid along body 102. For example, the inner needle 122 may remain in position as the outer needle 120 is advanced until the distal tips of the inner needle and outer needle substantially align. Afterwards, advancement of the outer needle 120 may cause the inner needle 122 to also advance so that the distal tips of the inner needle 122 and outer needle 120 remain substantially aligned. In other embodiments, the retraction of inner needle 122 may be a manual process that is performed by a physician, such as by holding the second trigger mechanism 108 in place as first trigger mechanism 106 is slid distally along body 102, or by sliding second trigger mechanism 108 proximally along body 102. As shown in FIG. 5B and as described herein, outer needle 122 bends or curves away from an axis of the lumen of elongate shaft 110 as the outer needle 120 is advanced distally away from the distal end of elongate shaft 110. The distal end of outer needle 120 may be advanced away from the distal end of elongate shaft 110 until the distal end of outer needle 120 (and the distal end of inner needle 122) is positioned adjacent tissue to be penetrated with inner needle 122. As described herein, the outer needle 120 is made of a flexible shape-memory material and has a preconfigured curved that may be configured or selected to fit/accommodate a specific patient.

Figure 6A:
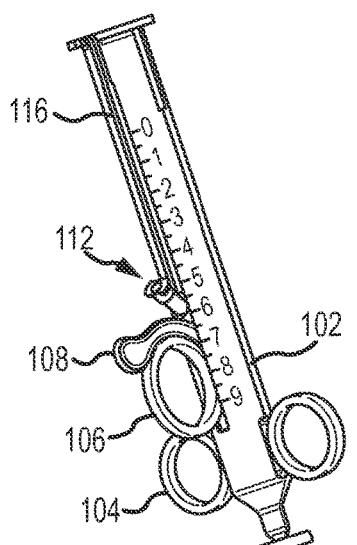
FIGS. 6A-6C illustrate the tissue penetrating device of FIG. 1 with the outer needle extending from the elongate shaft and with the inner needle extending from the outer needle according to an embodiment.
Figure 6B:
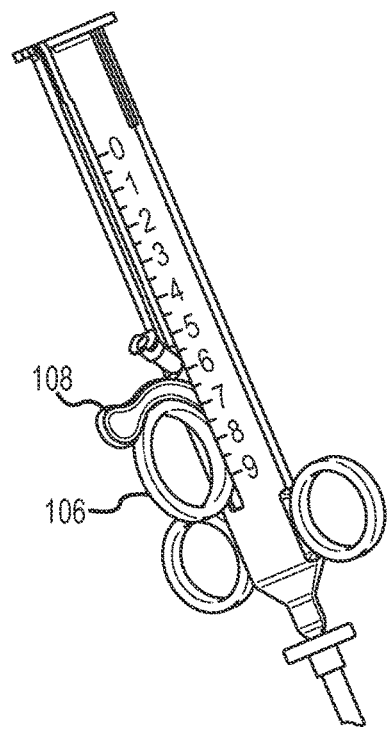
Figure 6C:
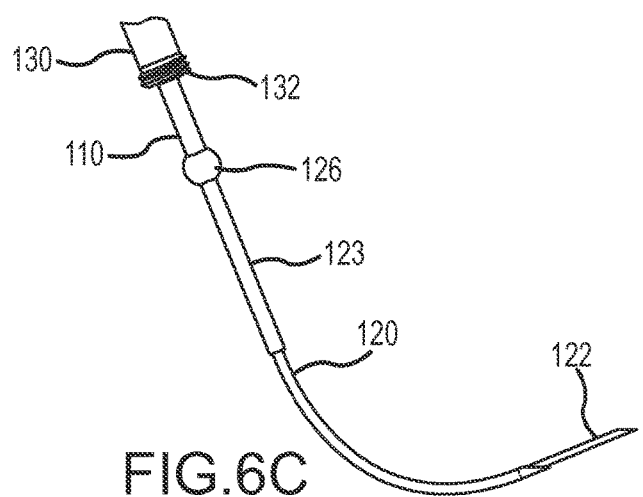

After the distal end of the outer needle 120, and inner needle 122, is positioned adjacent tissue to be penetrated with inner needle 122 (e.g., adjacent a septal wall), the second trigger mechanism 108 may be slid distally along body 102 to extend inner needle 122 beyond the distal end of outer needle 120 and thereby penetrate the patient's tissue. FIGS. 6A-6C illustrate the second trigger mechanism 108 being slid distally along body 102 to extend inner needle 122 so as to penetrate tissue of the patient. FIG. 6A also illustrates a track 116 within which the first trigger mechanism 106 and/or second trigger mechanism 108 may slide.

FIGS. 6A-6C further illustrate a reinforcement sleeve 123 being slid over the outer needle 120. The reinforcement sleeve 123 may reinforce the outer needle 120 and/or inner needle 122 as the inner needle 122 is extended from the distal end of outer needle 120. Relatively substantial bending forces may be imparted to the outer needle 120 at or near where the outer needle 122 extends from the elongate shaft 110 as the inner needle 122 is being inserted through bodily tissue, such as through tough scar tissue. These bending forces may cause the outer needle 120 to bend or flex under the load, especially due to the outer needle 120 being made of the flexible shape-memory material. Flexing or bending of the outer needle 120 may hinder the inner needle's ability to penetrate the bodily tissue. Reinforcement sleeve 123 minimizes or greatly reduces bending or flexing of the outer needle 120 at or near where the outer needle 122 extends from the elongate shaft 110. Rather, the bending forces are imparted to the reinforcement sleeve 123, which may be made of stainless steel or another relatively rigid material that does readily bend or flex under load. In this manner, the outer needle 120 and inner needle 122 may be substantially reinforced as the inner needle 122 is extended from the flexed or curved outer needle 120.

In some embodiments, the reinforcement sleeve 123 may be extended up to near where the outer needle 120 begins to bend, flex, or otherwise curve. The reinforcement sleeve 123 may be configured to automatically extend from the distal end of the elongate shaft 110 with the outer needle 120, or may be extended separately therefrom. For example, operation of the first trigger mechanism 106 along body 102 may cause the outer needle 120 and reinforcement sleeve 123 to simultaneously extend from the distal end of elongate shaft 110. The reinforcement sleeve 123 may be deployed or extended via first trigger mechanism 106 up to near the location that the outer needle 120 begins to bend or flex, after which further operation of the first trigger mechanism 106 may cause the outer needle 120 to extend independent of the reinforcement sleeve 123. In other embodiments, a separate mechanism (not shown) may be used to deploy and retract reinforcement sleeve 123.

Figure 7B:
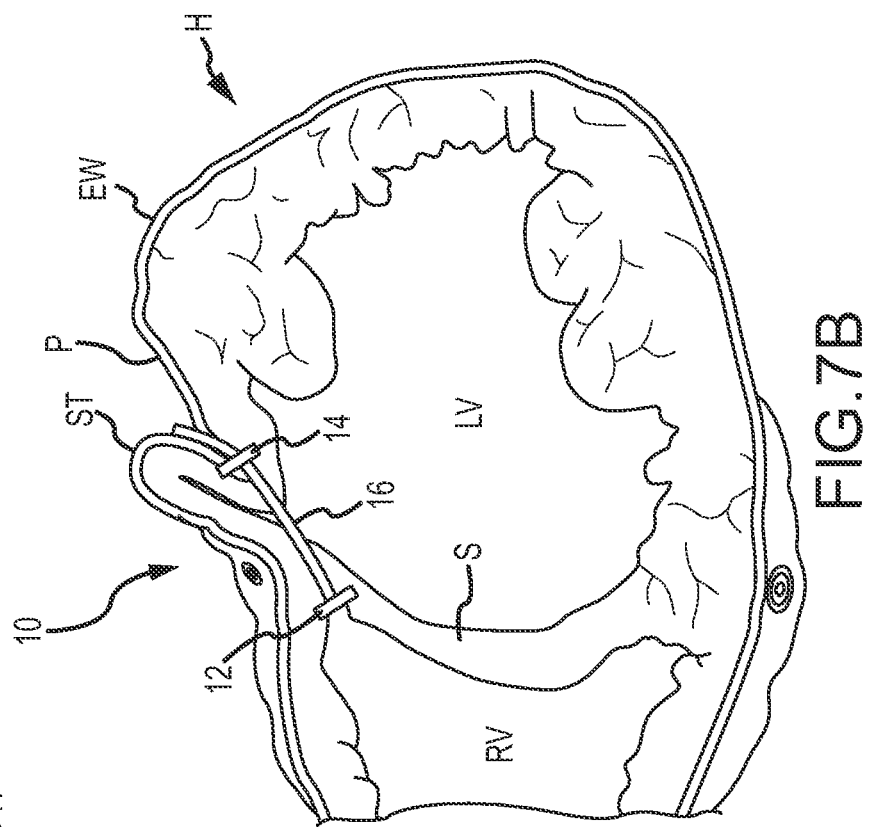
FIG. 7B illustrates a cross-sectional view of the heart of FIG. 7A, showing a reduction in the size of the left ventricle effected by one of the implants.
Figure 7A:
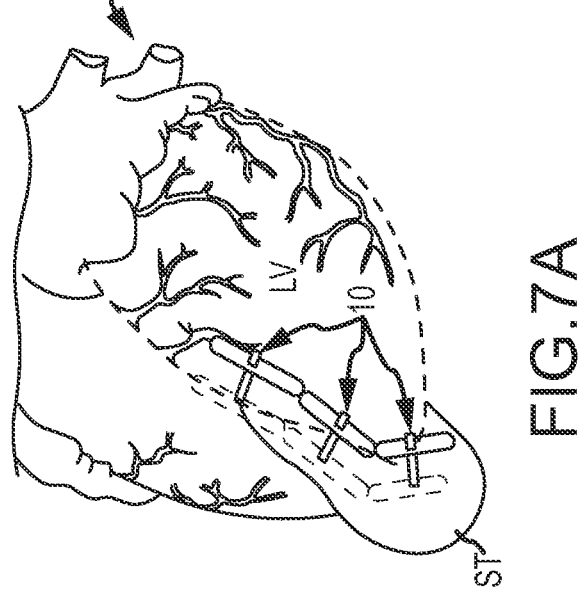
FIG. 7A illustrates a reconstructed left ventricle using a series of implanted anchors so as to mitigate the deleterious effects of congestive heart failure, according to an embodiment.

Referring now to FIGS. 7A-8I, a procedure for treating congestive heart failure using the tissue penetrating device 100 is illustrated. Specifically, FIGS. 7A and 7B illustrate a series of implants 10 implanted in a heart H so as to decrease a cross-section of a left ventricle LV. Each implant 10 generally includes a first anchor 12, a second anchor 14, and a tension member 16 coupling the anchors together. Tension in the tension member 16 is transferred from the anchors, 12 and 14, to the septum S and the external wall EW bordering the left ventricle LV so as to bring these structures into engagement, thereby effectively excluding a region of scar tissue ST from the left ventricle. In many embodiments described herein, implant 10 will be deployed by penetrating the external wall EW and septum S via a pericardium P of the heart H, and also by accessing a right ventricle RV via a right atrium. Anchors deployed within a right ventricle and/or in engagement with the septum S may sometimes be referred to herein as septal anchors, while anchors deployed along the external wall EW of the left ventricle LV may be referred to as epicardial anchors.

Figure 7C:
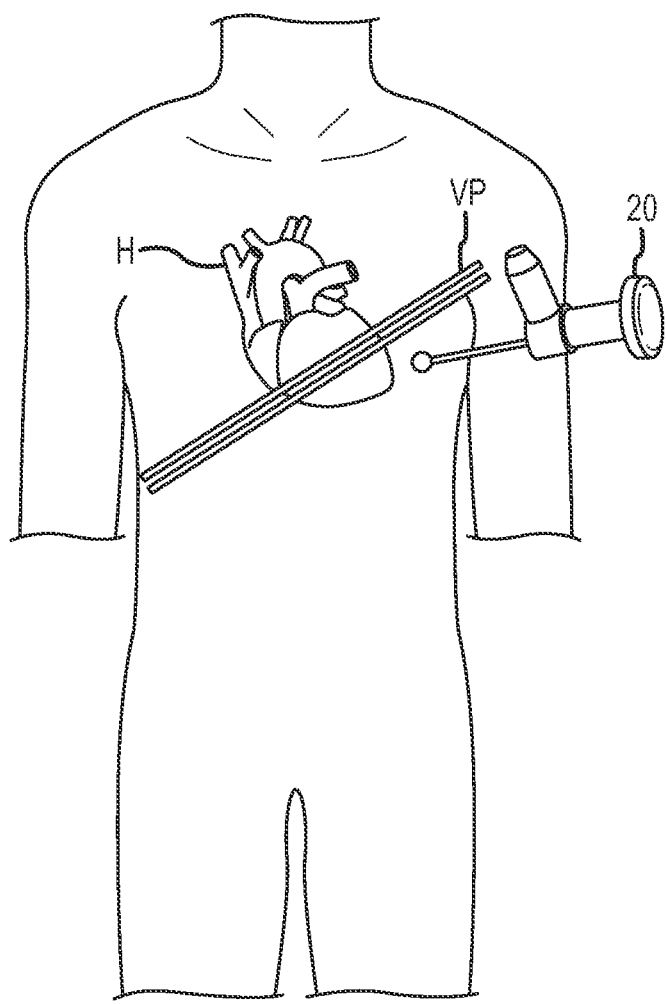
FIGS. 7C and 7D illustrate minimally invasive access to and endoscopic imaging of a pericardium of the heart.
Figure 7D:
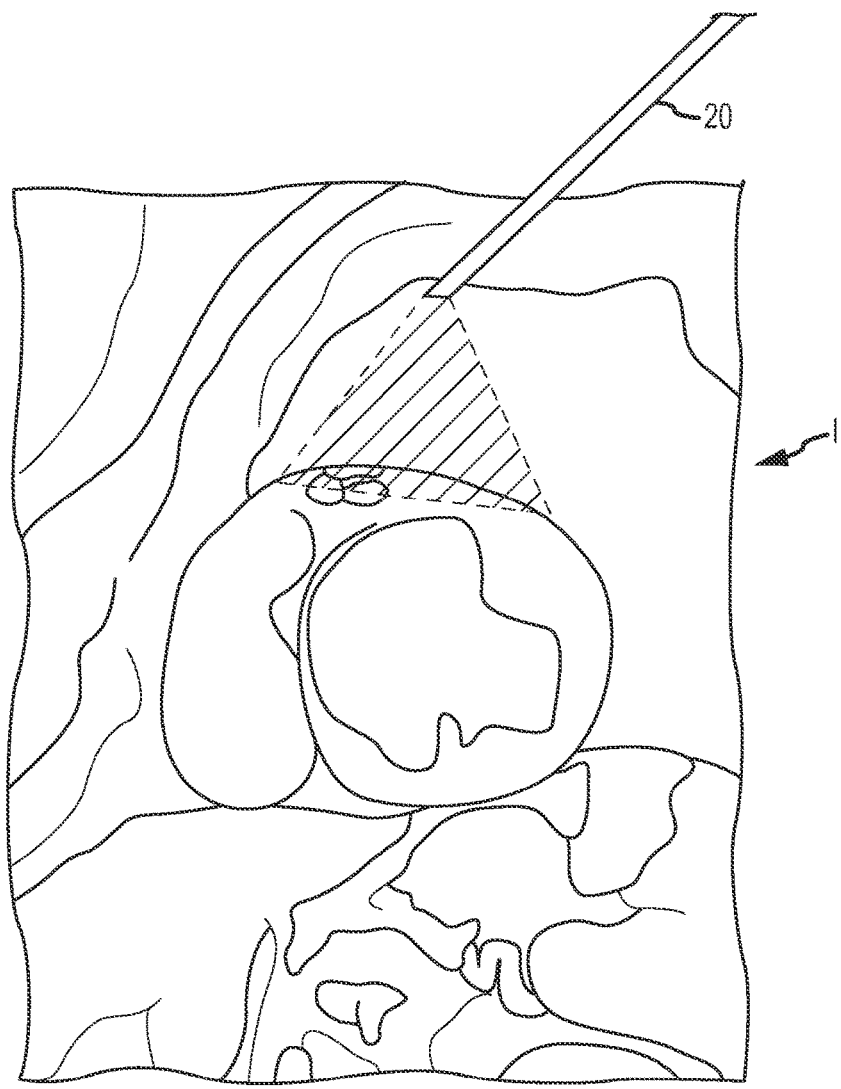

Referring now to FIGS. 7C and 7D an MRI image I taken along viewing plane VP schematically illustrates use of a thoracoscope or fluoroscope 20 to provide a field of view encompassing a region of the pericardium of the heart, with the region including a target site for deployment of one or more epicardial anchors and/or septal anchors of the implant system.

Figure 7E:
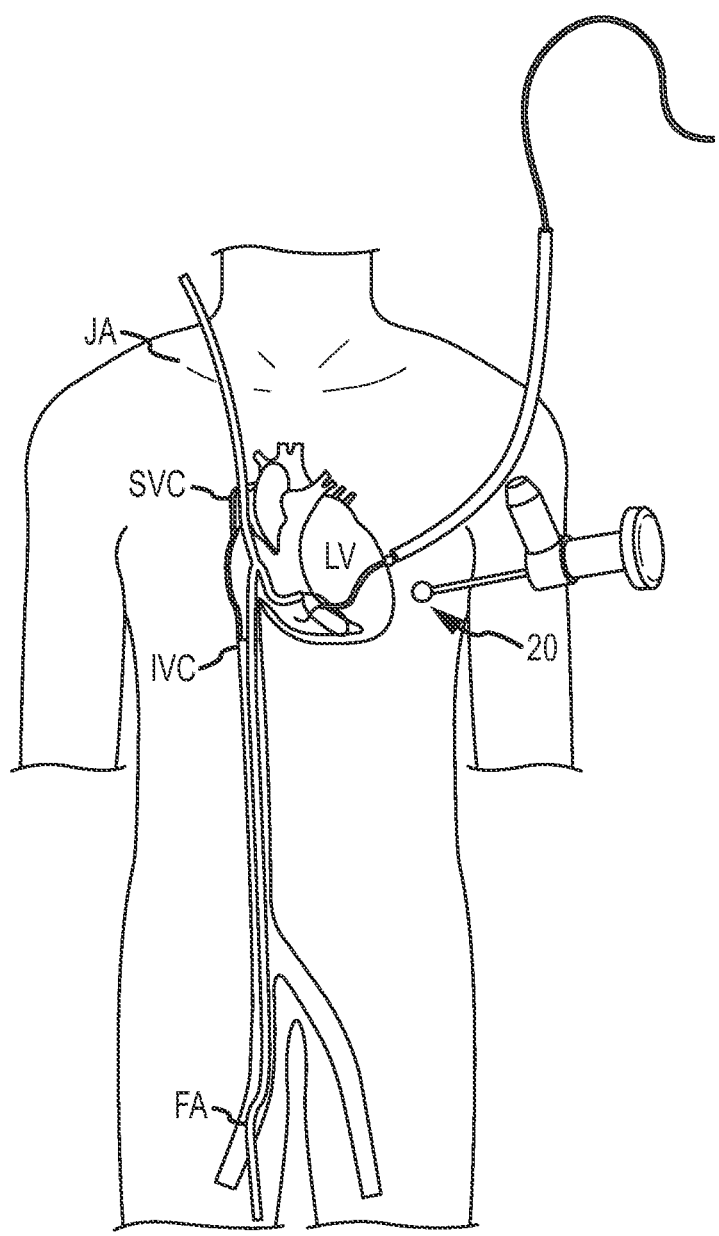
FIG. 7E illustrates joining of a femoral access tool path through the right atrium and an endoscopic trans-epicardial access tool path by snaring a guidewire within the right ventricle of the heart.

Referring now to FIG. 7E, joining of an access path through the right atrium to an access path through the pericardium and epicardium by snaring of a guidewire within the right ventricle under thoracoscopic/fluoroscopic guidance 20 is schematically illustrated. The right atrial access path may extend into the arterial vasculature via the femoral artery FA and inferior vena cava IVC, via the jugular artery JA via the superior vena cava, or the like. As can be understood with reference to FIG. 8A, a selected location for perforation of the external wall EW can be identified using an image from thoracoscope/fluoroscope 20, optionally in combination with an image from another imaging modality, such as a prior or contemporaneous image from an ultrasound imaging system, an MRI imaging system, an X-ray or fluoroscopic imaging system, a CT imaging system, or the like. In exemplary embodiments, a shaft 430 of an access tool having a working lumen there through is advanced through the epicardium of the beating heart so that a distal end of the shaft 430 is positioned adjacent the external wall EW of the heart. Shaft 430 may comprise a trocar and may have a proximal hemostasis valve at its proximal end so as to inhibit blood flow through the lumen and facilitate insertion and/or removal of elongate shaft 110 or outer sleeve 130 of tissue penetrating device 100. Alignment sleeve 131 may be used to align the shaft 110 or outer sleeve 130 of device 100 with shaft 430.

A catheter 404 is inserted into the arterial vasculature via the jugular artery JA and tricuspid valve; or in other embodiments, via the femoral artery FA and inferior vena cava IVC, via the superior vena cava, or the like. A snare device 402, such as a wire hoop or wire basket, is positioned against the septum S at or adjacent an insertion point for inner needle 122. Snare device 402 may be positioned against septum S by using an off-the-shelf steerable catheter 404. The snare device 402 may provide a target for inner needle 122. Snare device 402 may be easily visible via fluoroscopy 20 and provide a reference point for steering the inner needle 122 and/or outer needle 120. As described herein, the distal tip of inner needle 122 and/or outer needle 120 may be radiopaque so that the distal tip of either or both needles is easily visible with a fluoroscope 20.

Shaft 430 may be positioned adjacent the external wall EW by inserting the shaft 430 through an incision between ribs of the patient, such as between the fourth and fifth intercostal space. Although not shown in the figures, in some embodiments the tissue anchoring device may be inserted through a subxiphoid incision and positioned adjacent the external wall EW. The subxiphoid incision may be relatively small, such as a two or three finger incision. The tissue anchoring device may be coupled with the external wall EW and a distal end of the shaft 430, or a distal end of elongate shaft 110, may be coupled with the tissue anchoring device to attached and/or stabilize the shaft 430 and/or elongate shaft 110 adjacent the external wall EW. The thoracoscope/fluoroscope 20 may also be inserted through the subxiphoid incision.

Figure 8A:
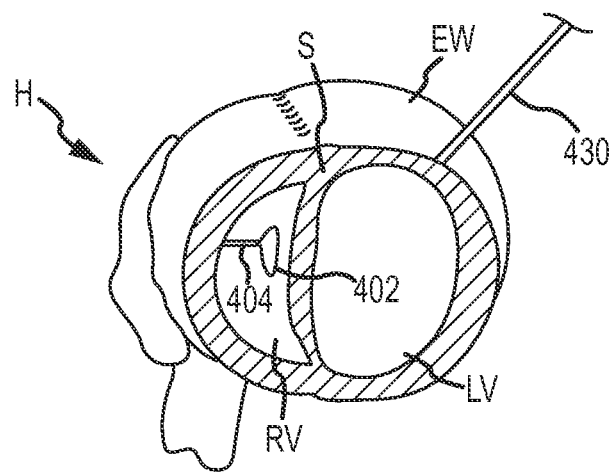
FIG. 8A illustrates a trocar or shaft positioned adjacent an external wall of a heart in a treatment for congestive heart failure according to an embodiment.
Figure 8B:
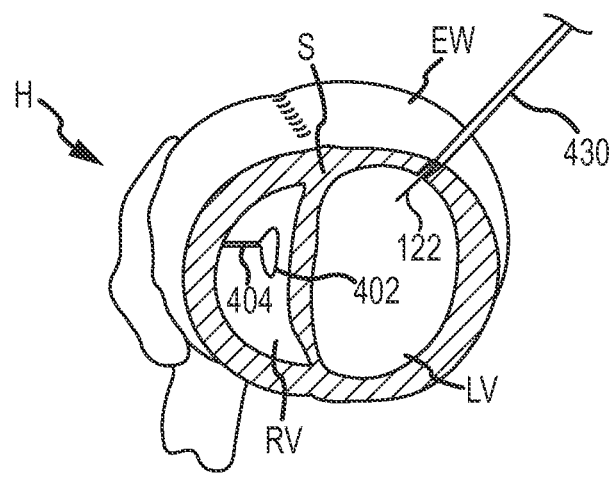
FIG. 8B illustrates an inner needle penetrating through the external wall of the heart in the congestive heart failure treatment.
Figure 8C:
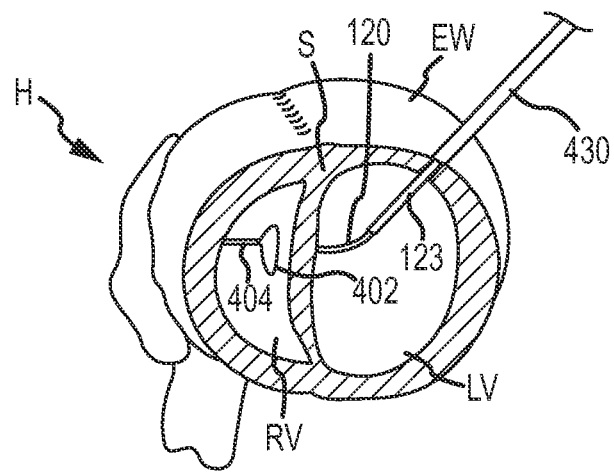
FIG. 8C illustrates an outer needle being positioned adjacent the septal wall of the heart in the congestive heart failure treatment.

As shown in FIG. 8B, with the shaft 430 positioned adjacent external wall EW, the second trigger mechanism 108 may be actuated so as to advance inner needle 122 from the lumens of elongate shaft 110 and outer needle 120 in order to penetrate the external wall EW. A pressure sensing element of inner needle 122 (e.g., fluid pathway, pressure transducer, and the like) may be used to determine that the inner needle 122 is positioned adjacent the external wall EW and/or inserted through the external wall EW and into the left ventricle LV. As shown in FIG. 8C, after the inner needle 122 is inserted through the external wall EW, the first trigger mechanism 106 may be actuated to extend the outer needle 120 distally of elongate shaft 110 and through external wall EW. The outer needle 120, and inner needle 122, may be advanced distally of elongate shaft 110 so that the outer needle 120 curves or bends away from an axis of the lumen of elongate shaft 110 and toward septum S. The inner needle 122 may be refracted within an outer needle 120 as the outer needle 120 is advanced toward septum S so as to prevent the inner needle 122 from penetrating other tissue of heart H. The outer needle 120 may be advanced until a distal end of outer needle 120 is positioned adjacent septum S. The pressure sensing element of inner needle 122 and/or of outer needle 120 may be used to determine that the distal tip of outer needle 120 is positioned adjacent septum S. FIG. 8C also illustrates the reinforcement sleeve 123 being extended distally of elongate shaft 110, either simultaneously with or independent of outer needle 120, to reinforce the outer needle 120 and inner needle 122 during subsequent penetration of bodily tissue, such as through tough scar tissue of the septum S.

Figure 8D:
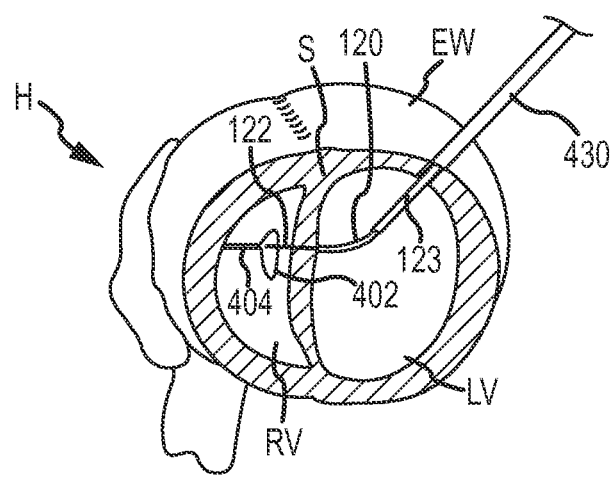
FIG. 8D illustrates the inner needle penetrating through the septal wall of the heart in the congestive heart failure treatment.
Figure 8E:
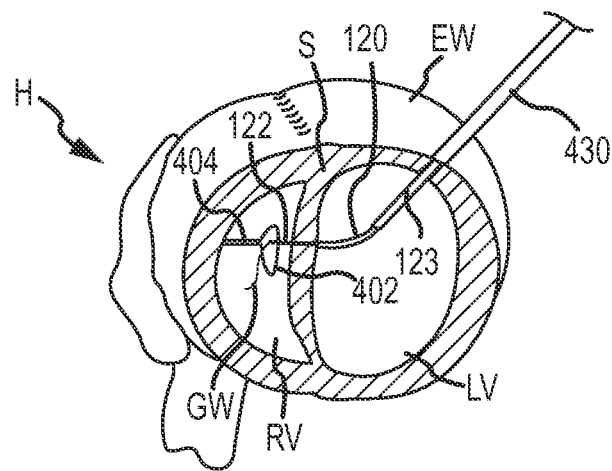
FIG. 8E illustrates a guidewire being inserted into the right ventricle of the heart so as to be snared by a snare device and join paths of the guidewire and snare device in the congestive heart failure treatment.

The snare device 402 and radiopaque distal tip of outer needle 120 and/or inner needle 122 may also be imaged via fluoroscope 20 to determine that the distal tip of outer needle 120 is near snare device 402. As described herein, as the outer needle 120 curves or bends as it is being distally advanced, the inner needle 122 is also forced to curve or bend along with outer needle 120. As shown in FIG. 8D, when the outer needle 120 and inner needle 122 are positioned adjacent septum S, the second trigger mechanism 108 may be actuated so as to advance inner needle 122 distally of outer needle 120 and penetrate the septal wall S. The inner needle 122 is inserted through septum S and into right ventricle RV so that the distal end of inner needle 122 is disposed within snare 402. As shown in FIG. 8E, the guidewire GW is then inserted through a lumen of inner needle 122 and into right ventricle RV. The snare device 402 may then be retracted within catheter 404 so that the snare device 402 snares the distal tip of inner needle 122 and/or guidewire GW. With the distal tip of inner needle 122 snared by snare device 402, the inner needle 122 and outer needle 120 may be retracted within elongate shaft 110 so that the guidewire GW remains snared within snare device 402.

Figure 8F:
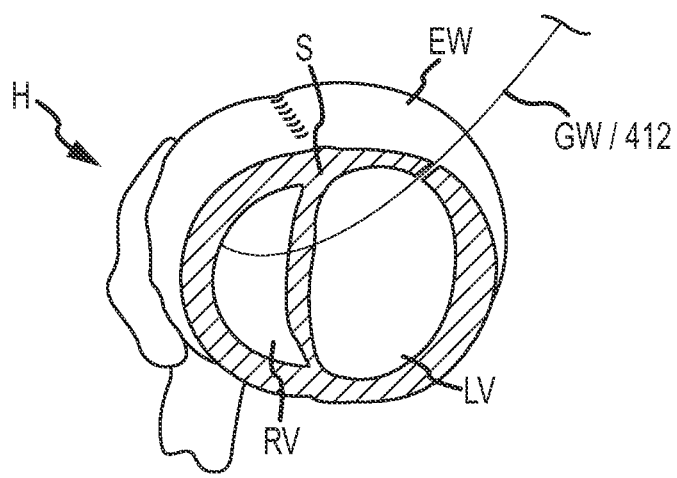
FIG. 8F illustrates the joined paths of the guidewire and snare device in the congestive heart failure treatment.

The inner needle 122, outer needle 120, and elongate shaft 110 may then be removed from the patient's body and the guidewire GW may be pulled through catheter 404 or retracted through septum S and external wall EW to a position outside the patient's body. As shown in FIG. 8F, in this manner, an insertion path of the guidewire GW and an insertion path of the catheter 404/snare device 402 may be joined so that the guidewire GW, or another wire, extends from a first point outside the patient's body, through the external wall EW, through the septum S, through the jugular artery JA or femoral artery FA, and outside the patient's body at a second and different point. With guidewire GW extending through heart H and outside the patient's body as described above, a tension member or tether 412 may be coupled with the guidewire GW and inserted through the jugular artery JA, into the right ventricle RV, through septum S and external wall EW, and out of the patient's body. FIG. 8F illustrates that the component inserted through heart H may represent the guidewire GW, the tension member 412, or both.

A septal anchor (i.e., 410 of FIGS. 8G-8I) is coupled with a distal end of tension member 412 so that as the tension member 412 is inserted through the jugular artery JA and through heart H, the septal anchor 410 is brought into position adjacent septum S. Exemplary embodiments of septal anchors 410 and tension members 412 are described in U.S. patent application Ser. No. 13/632,104, filed Sep. 30, 2012 and entitled "Trans-Catheter Ventricular Reconstruction Structures, Methods, and Systems for Treatment of Congestive Heart Failure and Other Conditions", the entire disclosure of which is incorporated herein by reference.

Figure 8G:
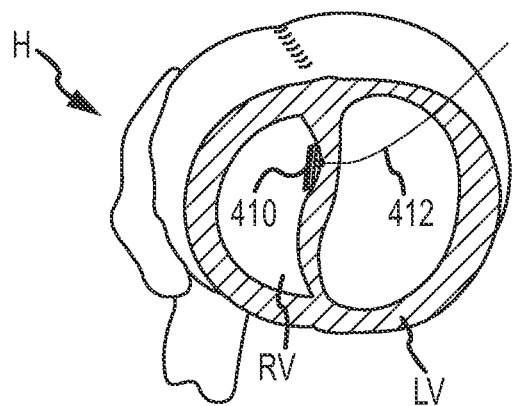
FIG. 8G illustrates a septal anchor positioned adjacent the septal wall and a tension member extending through the septal wall and external wall in the congestive heart failure treatment.
Figure 8H:
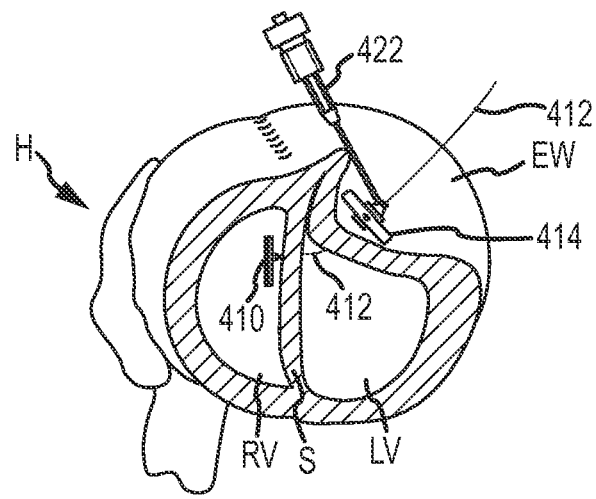
FIG. 8H illustrates an epicardial anchor being slid distally along the tension member and adjacent the external wall of the heart in the congestive heart failure treatment.

FIG. 8G illustrates the septal anchor 410 positioned adjacent septum S within right ventricle RV. Tension member 412 extends from septal anchor 410 through septum S into left ventricle LV and through external wall EW. FIG. 8H illustrates that an epicardial anchor 414 is coupled with tension member 412 and slid distally along tension member 412 until the epicardial anchor 414 is positioned adjacent external wall EW. An epicardial anchor application device 422 may be used to slide epicardial anchor 414 distally along tension member 412 to external wall EW. The epicardial anchor application device 422 may also be used to apply tension between septal anchor 410 and epicardial anchor 414 to urge or bring the septum S and external wall EW together. The epicardial anchor 414 may then be locked in place about tension member 412 to prevent the epicardial anchor 414 from moving about tension member 412 and to keep the septum S and external wall EW in position relative to one another. Exemplary embodiments of epicardial anchors 414 and epicardial anchor application devices 422 and uses thereof are described in U.S. patent application Ser. No. 13/632,104, which is incorporated by reference above.

Figure 8I:
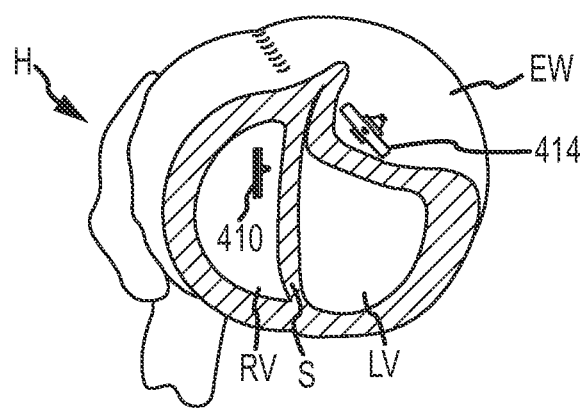
FIG. 8I illustrates the septal anchor and epicardial anchor being used to reconfigure the shape of the heart and the volume of the left ventricle in the congestive heart failure treatment.
Figure 9A:
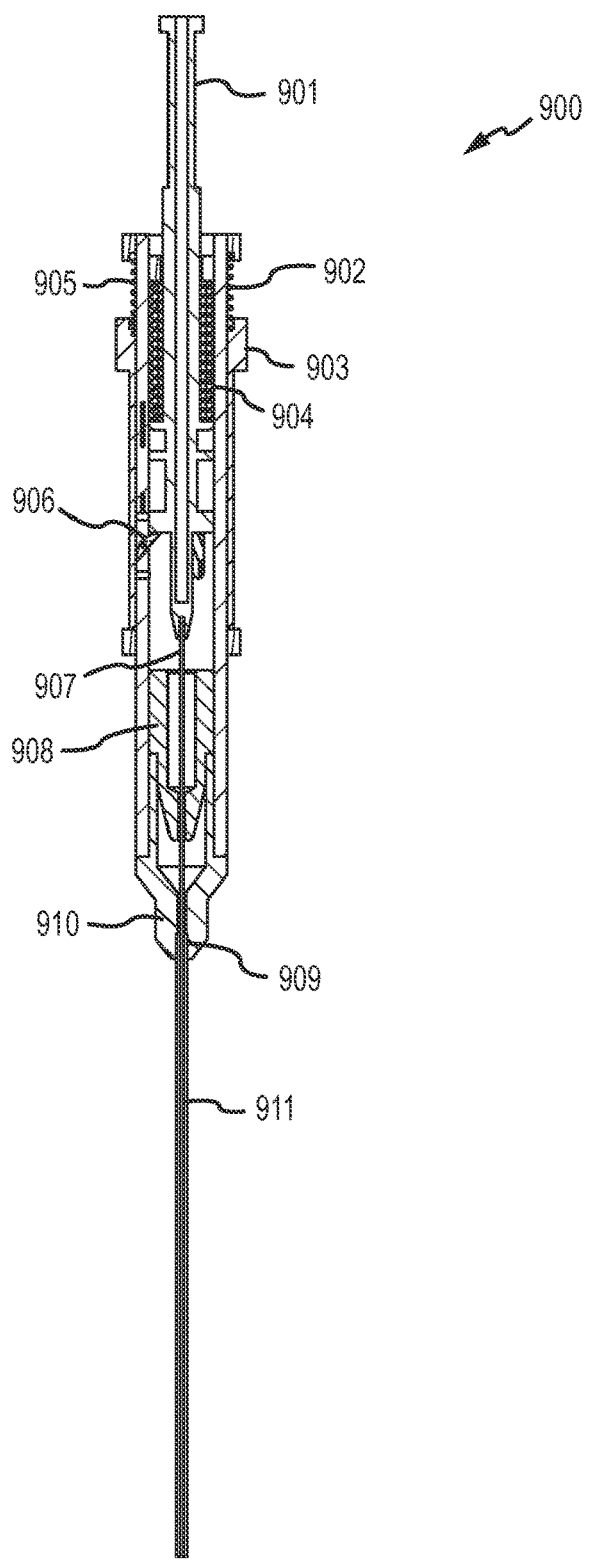
FIG. 9A illustrates a cross section view of a tissue penetrating device having a spring actuated triggering mechanism according to an embodiment.

As shown in FIG. 8I, after the septal anchor 410 and epicardial anchor 414 are tensioned so that the septum S and external wall EW are brought together, the tension member 412 proximal to epicardial anchor 414 may be cut and discarded. The septal anchor 410 and epicardial anchor 414 may be left in position relative to septum S and external wall EW with the heart H reconfigured to reduce a volume of left ventricle LV and exclude scar tissue from the left ventricle LV. The above process may be repeated a plurality of times to position additional septal anchors 410 and/or epicardial anchors 414 about the septum S and external wall EW. The anchors may be aligned about a desired contour of the heart, such as a contour defined by scar tissue and the like. In some embodiments, the contour for placement of multiple anchors may be determined via an image of the heart and insertion points for the anchors may be calculated or measured from the image. The insertion points may then be mapped or marked on the heart, such as by using a template or pattern. In this manner, the shape of heart H and the volume of left ventricle LV may be reconfigured as desired.

In some embodiments, deployment of multiple anchors about the septum S and/or external wall EW may be accomplished using multiple access ports and trocars or shafts, or multiple anchors may be deployed via the same access port. For example, in some embodiments the tissue penetrating device may be used to penetrate the external wall EW and/or septum S in multiple locations via the same access port. The tissue penetrating device is capable of delivering multiple penetrations via a single access port due, in part, to the bending or curving of the outer and inner needle. Further, in some embodiments the tissue penetrating device may be inserted through various incisions to penetrate the heart's tissue and deliver heart anchors, such as through incisions between ribs, subxiphoid incisions, and the like. In one embodiment, the tissue penetrating device may be inserted through a subxiphoid incision to penetrate heart tissue (e.g., external wall EW and/or Septum S) closer to the heart's apex while being inserted through an incision between the ribs to penetrate heart tissue located away from the apex.

In another embodiment, the process illustrated in FIGS. 8A-I may essentially occur in reverse. For example, the tissue penetrating device may be inserted into the arterial vasculature via the femoral artery FA and inferior vena cava IVC, via the jugular artery JA via the superior vena cava, or the like. In such embodiments, the elongate shaft 110 may be a catheter that is easily insertable and/or steerable through the patient's arteries and into the arterial vasculature. The catheter (i.e., elongate shaft 110) may then be inserted into the right ventricle RV via the tricuspid valve and the distal tip of the catheter may be positioned adjacent the septum S. The inner needle 122 may then be advanced distally of the catheter to penetrate through the septum S. The outer needle 120 may then be advanced through the septum S and advanced toward the external wall EW. The outer needle 120 may bend, flex, or curve as it is being advanced toward the external wall EW as described herein.

A snare device 402 may be positioned adjacent the external wall EW and may provide a target for placement of the distal tip of the outer needle 120 relative to the external wall EW of the left ventricle LV. The distal tip of the outer needle 120 may be positioned adjacent the external wall EW at or near the target position defined by the snare device 402 and the inner needle 122 may be advanced distally of the outer needle 120's distal end to penetrate through the external wall EW. The inner needle 122, and/or a guidewire GW inserted through the inner needle 122's lumen, may then be snared via snare device 402 so as to join a pathway of the guidewire GW and snare device 402 as described herein. Placement of the septal anchors and/or epicardial anchors may then be performed as described herein.

In some embodiments, the snare device 402 may be inserted through the external wall EW and into the left ventricle LV and the outer needle 120 may be advanced within the left ventricle LV toward the snare device 402. The outer needle 122 may be advanced within the left ventricle LV until it is able to be snared by snare device 402, after which the outer needle 120, inner needle 122, and/or guidewire GW may be snared to join access paths and deploy septal and/or epicardial anchors as described herein.

Although the tissue penetrating device is generally described herein as being used for treatment of congestive heart failure, it should be realized that the tissue penetrating device may be used for any procedure in which tissue is penetrated with a needle. For example, in some embodiments, the tissue penetrating device may be used in performing a biopsy of an organ or other tissue. The tissue penetrating device may allow a needle or coring device to be positioned around tissue within a patient in order to access tissue that is to be biopsied. Other applications of the tissue penetrating device are likewise possible.

Referring now to FIGS. 9A-9E, illustrated is an embodiment of a tissue penetrating device 900 having a spring actuated triggering mechanism. FIGS. 9B-9E illustrate enlarged cross section views of the device 900 showing the various components in greater detail. Tissue penetrating device 900 may be actuated to rapidly fire or deploy an outer needle and/or inner needle across the tissue of the patient, such as across an external wall EW or septal wall S. Device 900 includes a straight needle trigger rod 901 that may be actuated by a physician to rapidly deploy an inner and/or outer needle, and more commonly only an inner needle.

Device 900 includes an outer housing 902. Device 900 further includes a trigger release sleeve 903 that may be rotated to release trigger release tabs 906 via a window 913 (FIG. 9C) and thereby actuate trigger rod 901. In one embodiment, device 900 may include 3 trigger release tabs 906 and 3 windows 913. Device 900 additionally includes a trigger spring 904 that, upon actuation, causes trigger rod 901 to rapidly move distally relative to the other components of device 900. Device 900 also includes a spring 905 for trigger release sleeve 903. Device 900 additionally includes a straight or inner needle 907 that is rapidly fired or deployed upon actuation of trigger spring 904 and trigger rod 901. Device 900 also includes a curved or outer needle 909 and two needle inserts 908 and 910. An elongated shaft or sheath 911 is coupled with a distal end of insert 910 and includes a lumen within which outer needle 909 and inner needle 907 are coaxially aligned and slidably disposed. As shown in FIG. 9C, the trigger release tabs 906 may be pivotally coupled to housing 902 via a pivot pin 912 and may prevent distal movement of trigger rod 901 until released by rotating trigger release sleeve 903 and aligning trigger release tabs 906 with corresponding windows 913.

Rotating trigger release sleeve 903 so as to align trigger release tabs 906 with the corresponding windows 913 actuates trigger rod 901 and causes the trigger rod 901 to spring forward via trigger spring 904 until a distal end of trigger rod 901 contacts insert 908. The forward springing movement of trigger rod 901 causes inner needle 907 to rapidly deploy relative to outer needle 909 and elongate shaft 911 and thereby penetrate tissue adjacent a distal end of the elongate shaft 911 and/or outer needle 909. The trigger rod 901, trigger spring 904, and trigger release sleeve 903 may be reset for subsequent firing.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A tissue penetrating device comprising:
   an elongate shaft having a proximal end and a distal end and a lumen extending between the proximal end and the distal end, wherein the proximal end is positionable outside of a patient's body and the distal end is positionable within the patient's body;
   a first needle disposed within the lumen of the elongate shaft and extendable distally of the elongate shaft's distal end between a first orientation and a second orientation, the first needle having a proximal end and a distal end with a lumen extending between the proximal end and the distal end, wherein in the first orientation the first needle is disposed within the elongate shaft's lumen and is substantially aligned with an axis of the elongate shaft's lumen, and wherein in the second orientation the first needle is extended distally of the elongate shaft's distal end and bends away from the axis of the lumen; and
   a second needle disposed within the first needle's lumen, the second needle being extendable distally from a distal tip of the first needle when the first needle is positioned in the first orientation and being extendable distally from the distal tip of the first needle when the first needle is positioned in the second orientation so as to penetrate tissue of a patient, the second needle being retractable within the lumen of the first needle subsequent to penetration of the tissue so that the second needle is fully disposed within the first needle's lumen;
   wherein when the second needle is extended distally of the distal tip of the first needle, a distal end of the second needle is coaxially aligned with the distal tip of the first needle;
   wherein the first needle is made of a flexible shape-memory material having a preconfigured bend or curve such that the first needle bends or curves from the first orientation to the second orientation as the first needle is extended distally of the elongate shaft's distal end; and
   wherein the second needle comprises a proximal end and an open distal end with a lumen extending between the proximal end and the open distal end such that a guidewire is insertable through the lumen and through the open distal end of the second needle.

2. The tissue penetrating device of claim 1, wherein the second needle is configured to measure or monitor fluid pressure within the patient's body.

3. The tissue penetrating device of claim 2, wherein the fluid pressure is measured or monitored so as to determine a location within a heart chamber of the patient.

4. The tissue penetrating device of claim 1, further comprising a tool body positioned at the proximal end of the elongate shaft, the tool body being configured to be grasped by a physician to enable the physician to extend the first needle and the second needle to penetrate the patient's tissue.

5. The tissue penetrating device of claim 4, wherein the tool body comprises a first trigger member that is slidable axially along the tool body to extend and retract the first needle relative to the elongate shaft's distal end.

6. The tissue penetrating device of claim 5, wherein the tool body further comprises a second trigger member that is operable independent of the first trigger member, the second trigger member being slidable axially along the tool body to extend and retract the second needle relative to the first needle.

7. The tissue penetrating device of claim 4, wherein the tool body comprises a spring trigger mechanism that causes the first needle or the second needle to rapidly deploy distally upon actuation of the spring trigger mechanism.

8. The tissue penetrating device of claim 1, wherein the distal end of the elongate shaft comprises a locking mechanism that is couplable with an attachment device that is removably attachable to the patient's tissue.

9. The tissue penetrating device of claim 1, wherein when in the second orientation the first needle is bendable away from the axis of the lumen by between 45 and 210 degrees.

10. The tissue penetrating device of claim 1, wherein the distal end of the first needle or second needle comprises a pressure transducer or is configured to monitor fluid pressure.

11. The tissue penetrating device of claim 1, wherein the elongate shaft comprises a catheter.

12. A method of penetrating tissue of a patient, the method comprising:
  providing a tissue penetrating device comprising:
    an elongate shaft having a proximal end, a distal end, and a lumen extending between the proximal end and the distal end;
    a first needle disposed within the lumen of the elongate shaft and extendable distally of the elongate shaft's distal end between a first orientation and a second orientation, the first needle having a proximal end, a distal end, and a lumen extending between the proximal end and the distal end; and
    a second needle disposed within the first needle's lumen and extendable therefrom;
  advancing the first needle distally of the elongate shaft's distal end so as to position the first needle's distal end adjacent the patient's tissue, wherein the first needle bends away from an axis of the elongate shaft's lumen as the first needle extends distally of the elongate shaft's distal end;
  advancing the second needle distally of a distal tip of the first needle so as to penetrate the patient's tissue with the second needle; and
  advancing the first needle over the second needle and through the patient's tissue so that the second needle is retracted and fully disposed within the first needle's lumen;
  wherein when the second needle is extended distally of the distal tip of the first needle, a distal end of the second needle is coaxially aligned with the distal tip of the first needle; and
  wherein the first needle is made of a flexible shape-memory material having a preconfigured bend or curve such that the first needle bends or curves from the first orientation to the second orientation as the first needle is extended distally of the elongate shaft's distal end; and wherein in the second orientation, the first needle has a straight section that extends from the elongate shaft's distal end and that is axially aligned with the elongate shaft and a curved section that extends between the straight section and the distal end of the first needle.

13. The method of claim 12, wherein the second needle comprises a proximal end, a distal end, and a lumen extending between the proximal end, and wherein the method further comprises inserting a guidewire through the lumen of the second needle and into the patient's body.

14. The method of claim 12, wherein advancing the first needle comprises actuating a first trigger mechanism of a tool body, the tool body being positioned at the proximal end of the elongate shaft and being configured to be operated by a physician.

15. The method of claim 14, wherein advancing the second needle comprises actuating a second trigger mechanism of the tool body, the second trigger mechanism being operable independent of the first trigger mechanism.

16. The method of claim 15, wherein the first trigger mechanism or the second trigger mechanism comprises a spring trigger mechanism that causes the first needle or the second needle to deploy rapidly upon actuation of the spring trigger mechanism.

17. The method of claim 12, wherein the elongate shaft comprises a catheter.

18. A method of penetrating cardiac tissue for treatment of congestive heart failure, the method comprising:
  positioning a distal end of an elongate shaft adjacent an external wall of a patient's heart while a proximal end of the elongate shaft is positioned outside of the patient's body;
  advancing a needle distally of a distal end of the elongate shaft and through the external wall, the needle being disposed centrally within a lumen of a sleeve;
  advancing the sleeve distally of the distal end of the elongate shaft and over the needle through the external wall so that the needle is retracted and fully disposed within the lumen of the sleeve, the sleeve being initially disposed within a lumen of the elongate shaft and coaxially aligned with the needle prior to advancement of the sleeve through the external wall;
  advancing the sleeve distally of the external wall to position the sleeve and needle adjacent a septal wall of the patient's heart, wherein the sleeve is advanced adjacent the septal wall with the needle fully disposed within the lumen of the sleeve, and wherein the sleeve comprises a flexible shape-memory material having a preconfigured bend or curve such that the sleeve curves away from an axis of the elongate shaft's lumen as the sleeve is advanced distally of the distal end of the elongate shaft and distally of the external wall; and
  advancing the needle distally of a distal tip of the sleeve and through the septal wall of the patient's heart;
  wherein when the needle is advanced distally of the distal tip of the sleeve, a distal end of the needle is coaxially aligned with the distal tip of the sleeve; and
  wherein when the sleeve is fully advanced distally of the distal end of the elongate shaft, the sleeve has a straight section that extends from the elongate shaft's distal end and that is axially aligned with the elongate shaft's lumen and a curved section that extends between the straight section and the distal tip of the sleeve.

19. The method of claim 18, further comprising:

inserting a guidewire through a lumen of the needle and through the external wall and septal wall so that the guidewire is positioned within a chamber of the heart; and joining the guidewire with a snare that is inserted within the chamber of the heart along a path different than the guidewire, wherein joining the guidewire and the snare couples a path of the guidewire and the snare.

20. The method of claim 19, further comprising advancing a first anchor and an elongate tension member into the chamber along the joined paths, wherein the first anchor is positioned distally of the septal wall and wherein the tension member extends from distally of the septal wall, through the external wall and septal wall, and outside the patient's body.

21. The method of claim 20, further comprising:
coupling a second anchor to the tension member;
advancing the second anchor along the tension member to a position proximate the external wall; and
applying tension between the first anchor and the second anchor so that the anchors urge the septal wall and external wall to engage.

22. The method of claim 18, wherein the sleeve comprises an outer needle that is slidable over the needle and disposed within the elongate shaft's lumen.

23. The method of claim 18, further comprising sensing a pressure with a distal end of the needle or sleeve.

24. The method of claim 18, wherein the elongate shaft comprises a catheter.

* * * * *